US000001969H

(19) United States

(12) Statutory Invention Registration

Fell et al.

(10) Reg. No.: US H1969 H

(43) Published: Jun. 5, 2001

(54) ABSORBENT GARMENTS WITH MICROPOROUS FILMS HAVING ZONED BREATHABILITY

(75) Inventors: David Arthur Fell, Neenah; Sarah Jane Marie Freiburger, Kaukauna; Keith Joseph Renard, Oshkosh, all of WI (US)

(73) Assignee: Kimberly-Clark Worldwide, Inc., Neenah, WI (US)

(21) Appl. No.: 09/312,516

(22) Filed: May 14, 1999

(51) Int. Cl.[7] ..... A61F 13/15

(52) U.S. Cl. ..... 604/367; 604/385.1

(58) Field of Search ..... 604/385.1, 367

(56) References Cited

U.S. PATENT DOCUMENTS 5,843,056 * 12/1998 Good et al. ..... 604/367

* cited by examiner

*Primary Examiner*—Charles T. Jordan

*Assistant Examiner*—Aileen J. Baker

(74) *Attorney, Agent, or Firm*—Kimberly-Clark Worldwide, Inc.

(57) ABSTRACT

Breathable microporous films are provided having controlled regional breathability with thick high WVTR regions and thinner low WVTR regions. The zoned breathable microporous films can be made by selectively applying heat and pressure to the microporous film such as by feeding a microporous film through a pair of heated nip rollers with one of the rolls having a raised surface area.

41 Claims, 14 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ABSORBENT GARMENTS WITH MICROPOROUS FILMS HAVING ZONED BREATHABILITY

FIELD OF THE INVENTION

The present invention relates to absorbent garments incorporating breathable microporous films. More particularly, the present invention relates to absorbent garments incorporating breathable microporous films having zoned breathability and methods of making the same.

BACKGROUND OF THE INVENTION

Various types of garments are presently available for absorbing human discharge. Examples of these garments include baby diapers, feminine care products, incontinence garments and the like. Generally speaking, the basic structure of this class of garments requires a liquid pervious body-side liner, an absorbent pad containing one or more layers for receiving and absorbing the discharge, and a liquid impervious backing member for containing the discharge.

While some of these absorbent garments perform satisfactorily for their intended purpose, there remains the need to provide a more discrete absorbent garment that possesses improved comfort characteristics.

Heretofore, some absorbent garments for absorbing and containing human discharge have typically been bulky and somewhat uncomfortable. For example, such absorbent garments may comprise flat sheets folded up into a diaper-like configuration which are bulky, particularly in the crotch portion. Obviously, this style of absorbent garment is uncomfortable to wear, especially if the wearer is an active adult. In addition, the absorbent garments include a film material that serves as liquid impervious outer cover. However, such film material lacks breathability, causing the absorbent garments to be hot and uncomfortable. The skin becomes overly hydrated by the aqueous liquids (for example, perspiration) trapped against the skin by the non-breathable film, resulting in skin occlusion.

Thus, it becomes apparent that a need exists for an absorbent garment that improves the absorbent characteristics and the containment characteristics of the absorbent garment while still being comfortable to wear as well as promoting skin wellness and skin dryness.

Microporous films are "breathable" barriers in the sense that the film acts as a barrier to liquids and particulate matter but allows water vapor and air to pass therethrough. In addition, by achieving and maintaining high breathability it is possible to provide an article that is more comfortable to wear since the migration of water vapor through the fabric helps reduce and/or limit discomfort resulting from excess moisture trapped against the skin. Thus, such an article can potentially contribute to an overall improved skin wellness.

Accordingly, microporous films have become an important article of commerce, finding a wide variety of applications. For example, microporous films have been used as backing members or as part of outer covers for personal care products such as diapers, training pants, incontinence garments, feminine hygiene products and the like. In addition, microporous films have likewise found use in protective apparel and infection control products such as surgical gowns, surgical drapes, protective workwear, wound dressings and bandages. Often microporous films are utilized as a multilayer laminate. The films can provide the desired barrier properties to the article while other materials laminated thereto can provide additional characteristics such as strength, abrasion resistance and/or good hand. For example, fibrous webs such as nonwoven fabrics allow the laminate to retain its breathability and can provide additional strength as well as an article having a cloth-like feel. Thus, microporous film laminates can be used in a variety of applications including, for example, those described above.

Although the breathability provided by microporous films and/or laminates thereof is advantageous in many articles, there exist some situations where high breathability can be undesirable. For example, in personal care articles such as diapers or incontinence garments the breathable barrier and absorbent core generally work together to retain bodily fluids (aqueous liquids) discharged into the garment. However, when aqueous liquid is retained within the absorbent core significantly higher levels of water vapor begin to pass through the breathable barrier. The increased levels of water vapor passing through the outer cover can form condensate on the outer portion of the garment. The condensate is simply water but can be perceived by the wearer as leakage. In addition, the condensate can create a damp uncomfortable feel to the outer portion of the garment which is unpleasant for those handling the article. It is believed that the skin wellness and/or improved comfort benefits of breathable outer covers are not achieved at areas directly adjacent the portion of the absorbent core retaining considerable amounts of liquid (e.g. typically those areas of the central or crotch region of the garment). Providing a breathable barrier which has less or limited breathability in such regions, while providing good breathability in the remaining regions, would provide a garment with excellent wearer comfort yet which limits the potential for outer cover dampness and odors. Thus, a breathable barrier that provides either zoned or controlled regional breathability is highly desirable.

Therefore, there exists a need for a breathable microporous film having regions with varied levels of breathability. In addition, there exists a need for such films which retain the desired barrier properties and which are capable of lamination to additional materials. Further, there exists a need for methods of making such films and in particular methods of reliably obtaining the desired levels of breathability in distinct regions of a film.

Thus, it becomes apparent that a need exists for a breathable absorbent garment that exhibits desired absorbency and containment characteristics of the garments while improving comfort during use.

SUMMARY OF THE INVENTION

The present invention provides an improved breathable absorbent garment having improved comfort characteristics. The breathable absorbent garment of the invention provides an absorbent pad disposed between a breathable backing member and a body-side liner. The breathable absorbent garment may also include an elasticized design that also facilitates the formation of the crotch section, as well as and effective seal between the garment and the wearer, whereby the garment is comfortable to wear.

The aforesaid needs are fulfilled and the problems experienced by those skilled in the art overcome by the film of present invention which, in one aspect, comprises a first microporous region having a thickness less than 100$\mu$ and a WVTR (also referred to as porosity) of at least 800 g/m$^2$/24 hours and a second region having a WVTR less than that of the first region wherein the WVTR of the second region is at least 15% less than the WVTR of the first region. The film has a hydrohead of at least about 50 mbar. The second region desirably has minimum dimensions of 5 cm by 5 cm and still more desirably comprises from about 5% to about 75% of the area of said film. In a further aspect, the first region can have a WVTR in excess of about 2500 g/m$^2$/24 hours and the second region a WVTR less than about 1500 g/m$^2$/24 hours. Additionally and/or alternatively, the second region can have a WVTR at least about 50% less than the WVTR of the first region. Further, the film can comprise a third region having a WVTR intermediate to that of the first and second regions. Still further, the film can comprise primarily of a thermoplastic polymer and in a further aspect, can comprise at least about 40% by weight filler and a thermoplastic polymer. One aspect of the present invention is to provide a microporous film having zoned breathability. Such a film reduces, and in some cases, prevents condensation on the outer surface of the breathable absorbent garment.

Further aspects of the present invention will appear in the description hereinafter.

Definitions

As used herein the term "nonwoven" fabric or web means a web having a structure of individual fibers or threads which are interlaid, but not in an identifiable manner as in a knitted or woven fabric. Nonwoven fabrics or webs have been formed by many processes such as for example, meltblowing processes, spunbonding processes, hydroentangling, air-laid and bonded carded web processes.

As used herein the term "spunbond fibers" refers to small diameter fibers of molecularly oriented polymeric material. Spunbond fibers may be formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, U.S. Pat. No. 5,382,400 to Pike et al.,and U.S. Pat. No. 5,759,926 to Pike et al. Spunbond fibers are generally not tacky when they are deposited onto a collecting surface and are generally continuous.

As used herein the term "meltblown fibers" means fibers of polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers may be continuous or discontinuous, are generally smaller than 10 microns in average diameter, and are generally tacky when deposited onto a collecting surface.

As used herein "multilayer nonwoven laminate" means a laminate of two or more nonwoven layers such as, for example, wherein some of the layers are spunbond and some meltblown such as a spunbond/meltblown/spunbond(SMS) laminate. Examples of multilayer nonwoven laminates are disclosed in U.S. Pat. No. 4,041,203 to Brock et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate such as by thermal point bonding as described below.

Alternatively, the fabric layers may be made individually, collected in rolls, and combined in a separate bonding step.

As used herein, the term "machine direction" or MD means the length of a fabric in the direction in which it is produced. The term "cross machine direction" or CD means the width of fabric, i.e. a direction generally perpendicular to the MD.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic and random symmetries.

As used herein, "ultrasonic bonding" means a process performed, for example, by passing the fabric between a sonic horn and anvil roll as illustrated in U.S. Pat. No. 4,374,888 to Bornslaeger.

As used herein "point bonding" means bonding one or more layers of fabric at numerous small, discrete bond points. For example, thermal point bonding generally involves passing one or more layers to be bonded between heated rolls such as, for example an engraved pattern roll and a smooth calender roll. The engraved roll is patterned in some way so that the entire fabric is not bonded over its entire surface, and the anvil roll is usually flat. As a result, various patterns for engraved rolls have been developed for functional as well as aesthetic reasons. One example of a pattern has points and is the Hansen Pennings or "H&P" pattern with about a 30% bond area when new and with about 200 bonds/square inch as taught in U.S. Pat. No. 3,855,046 to Hansen et al.

As used herein, the term "barrier" means a film, laminate or other fabric which is relatively impervious to the transmission of liquids and which has a hydrohead of at least about 50 mbar. Hydrohead as used herein refers to a measure of the liquid barrier properties of a fabric measured in millibars (mbar) as described herein below. However, it should be noted that in many applications of barrier fabrics, it may be desirable that they have a hydrohead value greater than about 80 mbar, 150 mbar or even 200 mbar.

As used herein, the term "breathability" refers to the water vapor transmission rate (WVTR) of an area of fabric which is measured in grams of water per square meter per day (g/m$^2$/24 hours). The WVTR of a fabric is the water vapor transmission rate which, in one aspect, gives an indication of how comfortable a fabric would be to wear. WVTR can be measured as indicated below and the results are reported in grams/square meter/day.

As used herein the term "backsheet" refers to the aqueous liquid impervious protective layer on the garment side of a personal care product which prevents bodily exudates from escaping from the product.

As used herein the term "monocomponent" fiber refers to a fiber formed from one or more extruders using only one polymer. This is not meant to exclude fibers formed from one polymer to which additives have been added. As used herein the term "multicomponent fibers" refers to fibers which have been formed from at least two polymers extruded from separate extruders but spun together to form one fiber. Multicomponent fibers are also sometimes referred to as conjugate or bicomponent fibers. The polymers of a multicomponent fiber are arranged in substantially constantly positioned distinct zones across the cross-section of the fiber and extend continuously along the length of the fiber. The configuration of such a fiber may be, for example, a sheath/core arrangement wherein one polymer is surrounded by another or may be a side by side arrangement, a pie arrangement or an "islands-in-the-sea"type arrangement. Multicomponent fibers are taught in U.S. Pat. No. 5,108,820 to Kaneko et al., U.S. Pat. No. 4,795,668 to Krueger et al. and U.S. Pat. No. 5,336,552 to Strack et al. Conjugate fibers and methods of making them are also taught in U.S. Pat. No. 5,382,400 to Pike et al. and may be used to produce crimp in the fibers by using the differential crystallization properties of the two (or more) polymers. The fibers may also have various shapes such as those described in U.S. Pat. Nos. 5,277,976 to Hogle et al., U.S. Pat. No. 5,466,410 to Hills and 5,069,970 and 5,057,368 to Largman et al.

As used herein the term "blend" means a mixture of two or more polymers while the term "alloy" means a sub-class of blends wherein the components are immiscible but have been compatibilized.

As used herein the term "biconstituent fibers" or "multiconstituent" refers to fibers which have been formed from at least two polymers extruded from the same extruder as a blend. The term "blend" is defined above. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Bicomponent and biconstituent fibers are discussed in U.S. Pat. No. 5,294,482 to Gessner and in the textbook *Polymer Blends and Composites* by John A. Manson and Leslie H. Sperling, copyright 1976 by Plenum Press, a division of Plenum Publishing Corporation of New York, ISBN 0-306-30831-2, at pages 273 through 277.

As used herein, the term "scrim" means a lightweight fabric used as a backing material. Scrims are often used as the base fabric for coated or laminated products.

As used herein, the term "garment" means the same as the term "personal care product".

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets and the like.

As used herein, the term "personal care product" means personal hygiene oriented items such as diapers, training pants, absorbent underpants, adult incontinence products, feminine hygiene products, and the like.

DETAILED DESCRIPTION OF THE INVENTION

Figure 1:
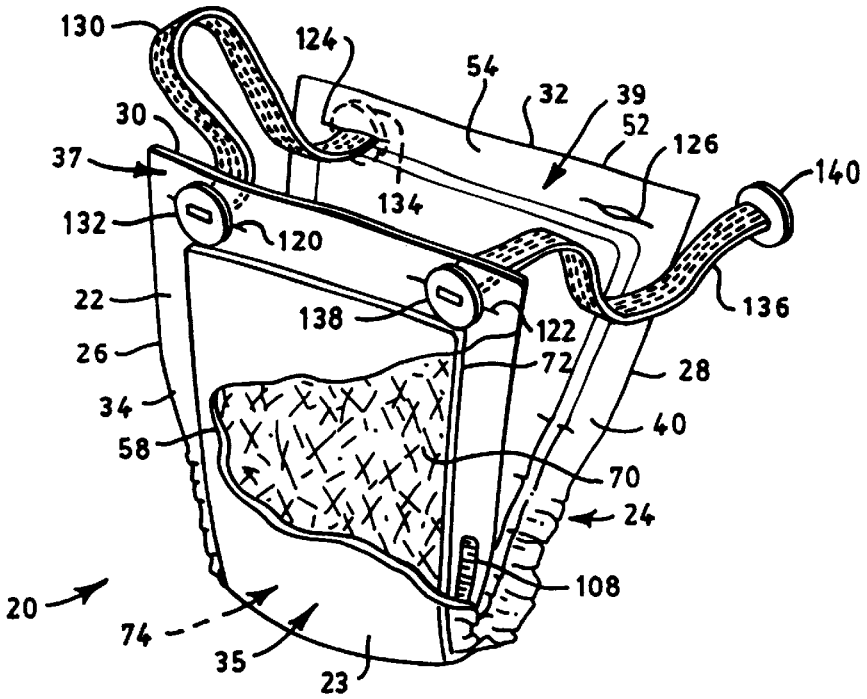
FIG. 1 is a perspective view of a specific embodiment of the invention with a portion of the liquid impervious backing member removed to expose the interior structure of the embodiment.

Referring to FIGS. 1 through 3*a,* there is illustrated one specific embodiment of the invention generally designated as 20, which presently is considered to be the best mode of practicing the invention. The breathable absorbent garment 20 includes a liquid impervious/vapor pervious backing member 22 that is of generally rectangular shape. The absorbent garment 20 has a peripheral edge 24 which includes side edges 26 and 28, a front edge 30 and a back edge 32. Throughout the specification, the term "generally rectangular" is used by the applicants. However, it is not intended that this term be limited to only a rectangular shape. But, instead, this term can include geometric shapes that are rectangular, oval or racetrack patterns, hourglass configurations, bilobal shapes, and in general any shape where the length is greater or less than the width.

The breathable absorbent garments 20 consists of the breathable backing member 22, a substantially liquid pervious body-side liner 40, and an absorbent pad 58 sandwiched between the backing member 22 and the body-side liner 40. The backing member 22 and the body-side liner 40 are desirably longer and wider than the absorbent pad 58, so that the peripheries of the backing member 22 and the body-side liner 40 form margins which may be sealed together using ultrasonic bonds, thermal bonds, adhesives, or other suitable means. In this sealed area, the leg elastics 96 and 108 may be incorporated between the backing member 22 and the body-side liner 40. The absorbent pad 58 may be attached to the backing member 22 and/or the body-side liner 40 using ultrasonic bonds, adhesives, or other suitable means. (See FIGS. 1, 2, and 3). In some embodiments, the breathable absorbent garments 20 also include an outer member 38. The outer member 38 is attached to the backing member 22 using ultrasonic bonds, adhesives, or other suitable means.

The breathable absorbent garment 20 can be constructed by supplying body-side liner 40 and backing member 22 materials and sandwiching an individual absorbent pad 58 between the backing member 22 and the body-side liner 40. The side and end peripheries of the backing member 22 and the body-side liner 40 outward of the absorbent pad 58 can be joined with the crotch region 35, the front waist region 37, and the back waist region 39 and sealed together. The absorbent pad 58 may optionally be T-shaped, I-shaped, oval-shaped, hourglass-shaped, rectangular-shaped, or irregularly-shaped. In addition, the absorbent core 58 may also include leg cutout, opposing indentations in the longitudinal side 62 and 64 of the absorbent pad 58. Leg cutout may improve the fit of the garment 20 as the reduced bulk between the wearer's legs reduces or prevents gapping thereby preventing leaks as well as improving comfort. The other materials used in the garment 20, including but not limited to the body-side liner 40, the backing member 22, and the outer member 38 may also be shaped to include leg cutouts. However, in some embodiments, it may be desirable for the absorbent pad 58 to be shaped to include leg cutouts, and not shape the other materials, including the body-side liner 40, the backing member 22, and the outer member 38, to include leg cutouts.

The liquid impervious/vapor pervious backing member 22 has an exterior surface 34 that faces away from the wearer and an interior surface 36 that faces toward the wearer. In construction of the breathable absorbent garment 20, the backing member 22, acting as a barrier, should retard the movement of the liquid through the breathable absorbent garment 20 by making the backing member 22 resistant to liquid penetration normally encountered under wearing conditions while remaining pervious to water vapor. The backing member 22 desirably comprises a material that is formed or treated to be aqueous liquid impervious. Alternatively, the backing member 22 may comprise a aqueous liquid pervious material and other suitable means (not shown), such as a aqueous liquid impervious/vapor pervious layer associated with the absorbent pad 58 may be provided to impede aqueous liquid movement away from the absorbent pad 58.

The backing member 22 may comprise a thin, liquid impervious/vapor pervious web or sheet of plastic film such as polyethylene, polypropylene, or polyolefin copolymers such as ethylene vinyl acetate, ethylene methylacrylate, ethylene ethyl acrylate, polyvinyl chloride, Nylon and similar material. Other acceptable materials include a single spunbonded layer of the above types of materials, two layers of spunbonded and meltblown materials or a three-layer material of spunbonded- meltblown-spunbonded material. Suitable foam materials may also be used, as well as materials that are both aqueous liquid impervious and vapor-pervious.

Alternately, the backing member 22 may comprise a nonwoven, fibrous web which has been suitably constructed and arranged to have low liquid perviousness. Still alternately, the backing member 22 may comprise a layered or laminated material, such as a thermally bonded plastic film and nonwoven web composite. More preferred, the backing member 22 has a water vapor transmission rate of at least about 500 grams/$m^2$/24 hours measured by ASTM E96-92. One example of a suitable film is a 39.4 grams per square meter microporous film produced by Mitsui and sold by Consolidated Thermoplastics (CT) under the tradename of ESPOIR® N-TAF-CT.

The term "liquid impervious" as used herein to describe a layer or laminate means that aqueous liquid such as urine will not pass through the layer or laminate under ordinary use conditions in a direction generally perpendicular to the plane of the layer or laminate at the point of the aqueous liquid contact.

The backing member 22 is needed to prevent liquid strike through to the outer clothing when discharge occurs onto the absorbent pad 58 of the breathable absorbent garment 20. The backing member 22 is located on the inside of the outer member 38 of the breathable absorbent garment 20 and typically consists of an aqueous liquid impervious film such as polyethylene. Use of only the film (without the outer member 38) may not be durable enough to withstand extended periods of wear. The absorbent pad 58 may be associated with a backing member 22 which may or may not include elastic characteristics.

In another embodiment of the present invention, the breathable absorbent garment 20 includes an aqueous liquid pervious body-side liner 40 and a substantially aqueous liquid impervious breathable backing member 22 superposed on the outer member 38. (See FIG. 3.) The absorbent pad 58 is sandwiched between the backing member 22 and the body-side liner 40. (See FIGS. 1, 2, 3, and 3*a*.) The backing member 22 and the body-side liner 40 are desirably longer and wider than the absorbent pad 58. The body-side liner 40 is designed to be positioned toward the wearer and is referred to as the body-facing surface 21 of the breathable absorbent garment 20. Conversely, the backing member 22 is designed to be positioned toward the outer member 38 and the outer clothing of the wearer and is referred to as the garment-facing surface 23 of the breathable absorbent garment 20.

The outer member 38 is compliant and soft feeling to the wearer. The outer member 38 may be any soft, flexible, porous sheet which is liquid pervious, permitting liquids to readily penetrate into its thickness, or impervious, resistant to the penetration of liquids into its thickness. A suitable outer member 38 may be manufactured from a wide range of materials, such as natural fibers (e.g., wood or cotton fibers), synthetic fibers (e.g., polyester or polypropylene fibers) or from a combination of natural and synthetic fibers or reticulated foams and apertured plastic films.

There are a number of manufacturing techniques which may be used to manufacture the outer member 38. Generally, the composition of the fibrous layer may be selected to achieve the desired properties, i.e. hand, aesthetics, tensile strength, cost, abrasion resistance, hook engagement, etc. It is understood that the bonding means used to attach the fabric layer to the microporous film should not impair the breathability of the microporous film. This concern is not as great in areas where reduced WVTR is desired.

For example, the outer member 38 may be woven or nonwoven web or sheet such as a spunbond, meltblown or bonded-carded web composed of synthetic polymer filaments, such as polypropylene, polyethylene, polyesters or the like, or a web of natural polymer filaments such as rayon or cotton. The bonded-carded web may be thermally bonded or sprayed with a binder by means well known to those skilled in the fabric art. Suitably, the outer member 38 is a nonwoven spunbond. Ideally, the outer member 38 is a spunbond polypropylene nonwoven with a wireweave bond pattern. Suitably, the spunbond material is available from Kimberly-Clark Corporation, located in Roswell, GA. The outer member 38 has a weight from about 0.3 oz. per square yard (osy) to about 2.0 osy and alternatively about 0.6 osy. The outer member 38 of the absorbent garment 20 maybe printed, colored or decoratively embossed. The outer member 38 has a pore size that readily allows the passage therethrough of air, sweat, perspiration, and water vapor due to the breathability of the material. The outer member 38 may be selectively embossed or perforated with discrete slits or holes extending therethrough.

The breathable absorbent garment 20 further includes a generally rectangular liquid pervious body-side liner 40 that is of approximately the same dimension as liquid impervious backing member 22. Liquid pervious body-side liner 40 has a peripheral edge 42 comprising a front edge 44, a back edge 46, and side edges 48 and 50. Liquid pervious body-side liner 40 has an exterior surface 52 that faces away from the wearer and an interior surface 54 that faces towards the wearer.

The body-side liner 40 is formed of an aqueous liquid pervious material so that aqueous liquid waste, and possibly semi-solid waste as well, can pass through to the absorbent pad 58 and be absorbed by the absorbent pad 58). A suitable body-side liner 40 may be comprised a nonwoven web, a spunbond, meltblown or bonded-carded web composed of synthetic polymer filaments or fibers, such as polypropylene, polyethylene, polyesters or the like, a perforated film, or a web or natural polymer filaments or fibers such as rayon or cotton. In addition, the body-side liner 40 may be treated with a surfactant to aid in aqueous liquid transfer. Suitably, the body-side liner 40 is a nonwoven spunbond. Ideally, the body-side liner 40 is a spunbond polypropylene nonwoven with a wireweave bond pattern. Suitably, the spunbond material is available from Kimberly-Clark Corporation, located in Roswell, Ga. The body-side liner 40 has a weight from about 0.3 oz. per square yard (osy) to about 2.0 osy and preferably about 0.5 osy. The body-side liner 40 of the absorbent garment maybe printed, colored or decoratively embossed. The body-side liner 40 has a pore size that readily allows the passage therethrough of air, sweat, perspiration due to the breathability of the material. The body-side liner 40 may be selectively embossed or perforated with discrete slits or holes extending therethrough.

The fabric is surface treated with a surfactant commercially available from Union Carbide Chemicals and Plastics Company, Inc., of Danbury, Conn., U.S.A. under the trade designation TRITON X-102. As used herein, the term "fabric" refers to all of the woven, knitted and nonwoven fibrous webs. The term "nonwoven web" means a web of material that is formed without the aid of a textile weaving or knitting process.

The liquid impervious backing member 22 and liquid pervious body-side liner 40 are joined near their respective peripheral edges 24 and 42 to form what can be considered to be a container, generally designated as 74, that defines an interior volume. This interior volume contains the remaining structure of the breathable absorbent garment 20, which comprises an absorbent pad 58.

The liquid impervious backing member 22 and the liquid pervious body-side liner 40 have essentially the same width and length. The width of backing member 22 and the body-side liner 40 ranges between about 4 inches (10.2 cm) and about 10 inches (25.4 cm) and, more preferably between about 5 inches (12.7 cm) and about 10 inches (25.4 cm) and about 27 inches (68.6 cm). The length of backing member 22 and the body-side liner 40 ranges between about 20 inches (50.8 cm) and about 30 inches (76.2 cm), more preferably between 21 inches (53.3 cm) and about 29 inches (73.7 cm), and most preferably between about 23 inches (58.4 cm) and about 28 inches (71.1 cm). In the specific embodiment of the invention as illustrated in FIGS. 1–4, the width of the backing member 22 and body-side liner 40 is about 9 inches (22.9 cm), and the length is about 27 inches ( 68.6 cm).

The absorbent pad 58 is of a generally rectangular shape and includes a peripheral edge 60 comprised of side edges 62 and 64, a front end edge 66 and a back end edge 68. The absorbent pad 58 has an exterior surface 70 that faces away from the wearer, and an interior surface 72 that faces towards the wearer.

The absorbent pad 58 comprises materials adapted to absorb and retain urine, menses, blood, or other body exudates. The absorbent pad 58 may comprise various natural or synthetic absorbent materials, such as cellulose fibers, surfactant treated meltblown fibers, wood pulp fibers, regenerated cellulose or cotton fibers, a blend of pulp and other fiber, chemically stiffened cellulose fibers, or the like. One such material is a coform material which is composed of a mixture of cellulosic fibers and synthetic polymer fibers. The absorbent pad 58 may also include compounds to increase its absorbency, such as 0–95 weight percent of organic or inorganic high-absorbency materials, which are typically capable of absorbing at least about 15 and desirably more that 25 times their weight in water. Suitable high-absorbency materials are described in U.S. Pat. Nos. 4,699,823 issued Oct. 13, 1987, to Kellenberger et at. and 5,147,343 issued Sep. 15, 1992 to Kellenberger, which are incorporated herein by reference. High absorbency materials are available from various commercial vendors, such as Dow Chemical Company, Hoechst Celanese Corporation, Stockhausen, Inc., and Allied Colloids, Inc. The absorbent pad 58 may also include tissue layers or acquisition or distribution layers to help maintain the integrity of fibrous absorbents, to facilitate liquid intake, and to transport liquid within the absorbent pad 58.

The breathable absorbent garment 20 may also include additional components to assist in the acquisition, distribution, and storage of body exudates. For example, the breathable absorbent garment 20 may include a transport layer, such as described in U.S. Pat. No. 4,798,603 issued Jan. 17, 1989, to Meyer et al., or a surge management layer, such as described in U.S. Pat. No. 5,486,166 issued Jan. 23, 1996, to Bishop et al., U.S. Pat. No. 5,364,382 issued Nov. 15, 1994, to Latimer et al., and European Patent No. 0 539 703, granted Mar. 5, 1997, which the patents are incorporated herein by reference. Such layers are also referred to as acquisition/distributionlayers and surge layers.

Figure 3:
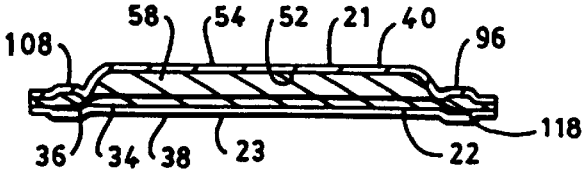
FIG. 3 is a cross-sectional view of the specific embodiment of FIG. 2 taken along section line 3—3 of FIG. 2.
Figure 3A:
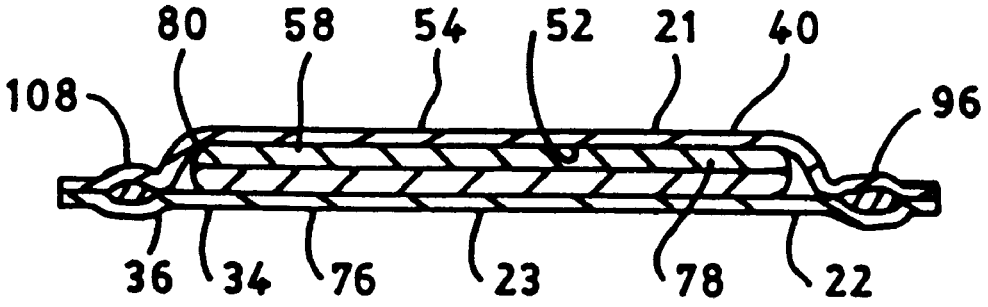
FIG. 3*a* is a cross-sectional view of an embodiment of FIG. 2 taken along section line 3—3 of FIG. 2.

One suitable absorbent pad 58 is separately illustrated in FIG. 3*a* and comprises an aqueous liquid storage layer 76 and an acquisition/distribution layer 78. The acquisition/distribution layer 78 has two sections. The 1st section, the acquisition section (not shown), has a greater aqueous liquid capacity per unit area with 479 gsm fluff pulp, such as CR1654 supplied by Alliance U.S. in Coosa Pines, Ala., and 260 gsm high absorbency material (herein also referred to as "SAP" or "SAM"). The acquisition section is centered in the area where urine will be insulted by the user. The second section (not shown) has lower capacity per unit area, 215 gsm fluff pulp and 117 gsm SAP.

The acquisition/distribution layer 78 is disposed on the aqueous liquid storage layer 76 toward the body-facing surface 21 of the absorbent pad 58 to help decelerate and diffuse surges of aqueous liquid that may be introduced into the absorbent pad 58. The acquisition/distribution layer 78 may comprise a through-air bonded carded web composed of a blend of 40 percent 6 denier polyester fibers, commercially available from Hoechst Celanese Corporation, and 60 percent 3 denier polypropylene/polyethylene sheath core bicomponent fibers, commercially available from the Chisso Corporation, with an overall basis weight ranging of from about 50 gsm and about 120 gsm. Alternative acquisition/distribution materials are described in U.S. Pat. No. 5,192,606 issued Mar. 9, 1993, to D. Proxmire et al.; U.S. Pat. No. 5,486,166 issued Jan. 23, 1996 to Ellis et al.; U.S. Pat. No. 5,490,846 issued Feb. 13, 1996 to Ellis et al.; and U.S. Pat. No. 5,509,915 issued Apr. 23, 1996 to Hanson et al.; the disclosures of which are hereby incorporated by reference. The illustrated acquisition/distribution layer 78 is rectangular with a length of about 305 mm. And a width of about 76 mm. The acquisition/distribution layer 78 can vary in shape and size as disclosed for the absorbent pad 58 and the breathable absorbent garment 20.

The pledget 140 (see FIGS. 4*a,* 4*b,* and 4*c*) is of a generally rectangular shape and has a peripheral edge 142 with a front edge 144, a back edge 146, and side edges 148 and 150. Pledget 140 has an exterior surface 152 facing away from the wearer and an interior surface 154 facing towards the wearer. The pledget 140 is dimensioned relative to the absorbent pad 58 such that its width and length are each less than the width and length of the absorbent pad 58, respectively. In this regard, the length of the pledget 140 is measured along the front and back edges 144 and 146 thereof and the width of the pledget 140 is measured along the side edges 148 and 150 thereof. The length of the absorbent pad 58 is measured along the front end and back end edges 66 and 68 and the width of the absorbent pad 58 is measured along the side edges 62 and 64.

The pledget 140 is most preferably made from a blend of fibers comprising about 15 to about 30 weight percent polypropylene or polyethylene fibers and about 85 to about 70 weight percent wood pulp fluff fibers, and has a basis weight of about 100 to about 525 gsm. In addition, a superabsorbent is added in an amount of about 10 to about 100 gsm. The pledget 140 may be formed on a tissue or a spunbonded carrier sheet, or may be formed without a carrier sheet.

The pledget 140 of the specific embodiment has a width equal to about 5.75 inches (14.6 cm) and a length equal to about 12 inches (30.5 cm). It is contemplated that the pledget 140 can have a width between about 3 inches (7.6 cm) and about 8.5 inches (21.6 cm), and a length between about 6 inches (15.2 cm) and about 14 inches (35.6 cm). The pledget 140 has a dry thickness equal to about 2.63 mm to about 17.5 mm.

The pledget 140 is illustrated in the drawings to have a dry thickness that is approximately equal to the dry thickness of the absorbent pad 58. However, it should be appreciated that the pledget 140 and absorbent pad 58 can be of different thicknesses. For example, the pledget 140 can be from about one-half to about four time the thickness of the absorbent pad 58.

The pledget 140 can be positioned so as to be symmetrical about the central longitudinal and transverse axes A—A, B—B, respectively, of the breathable absorbent garment 20. When in this position, the front and back edges 144 and 146 of pledget 140 are equi-distant from the front and back edges 44 and 46 of the body-side liner 40, respectively, and the side edges 148 and 150 of pledget 140 are equi-distant from the side edges 48 and 50 of the body-side liner 40, respectively. Further, when in this position, the absorbent pad 58 extends past the peripheral edge of the pledget 140.

Figure 4C:
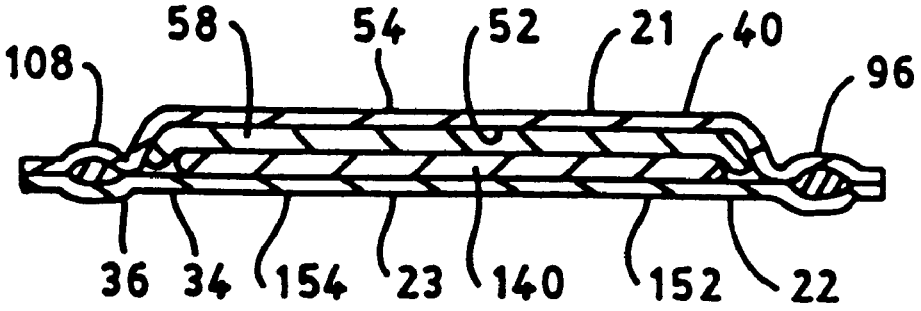
FIG. 4*c* is a cross-sectional view of the specific embodiment of FIG. 4*b* taken along section line 3—3 of FIG. 4*b;*
Figure 4A:
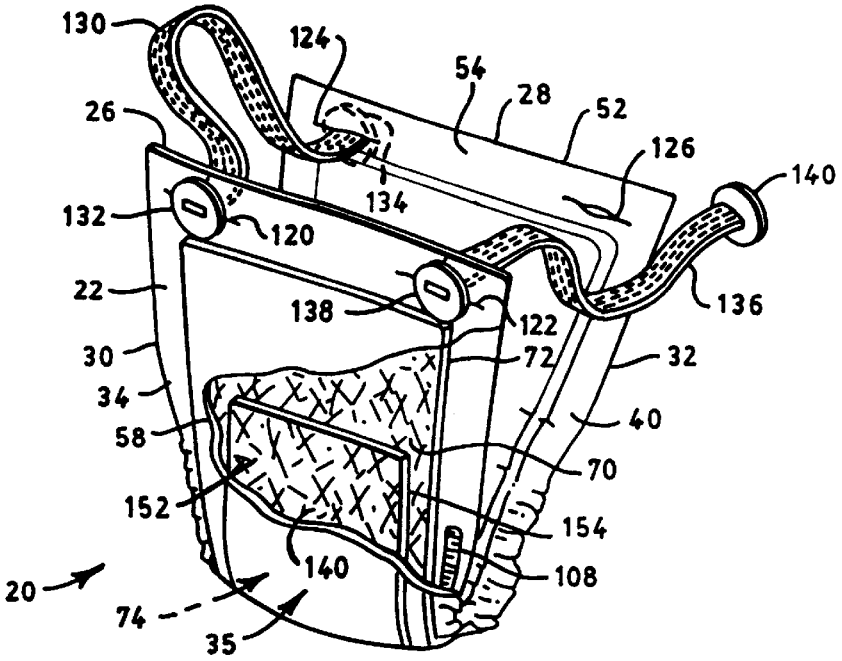
FIG. 4*a* is a perspective view of a specific embodiment of the invention with a portion of the liquid impervious backing member removed to expose the interior structure of the embodiment.
Figure 4B:
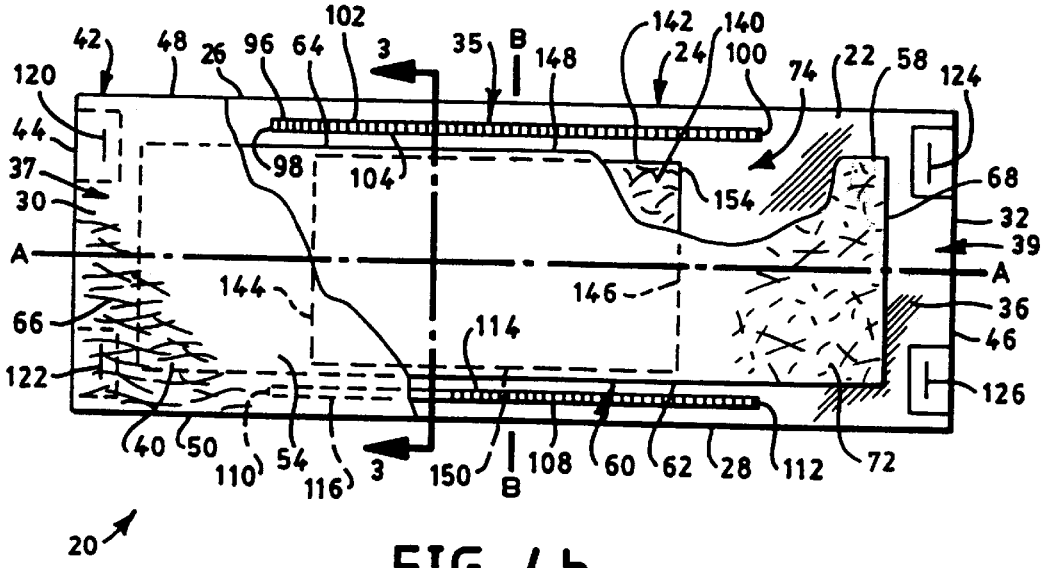
FIG. 4*b* is a plan view of the specific embodiment of FIG. 4*a* in an extended condition with the liquid pervious liner facing the viewer, and a portion of the liquid pervious liner and a portion of the absorbent pad removed.

The pledget 140 can, however, as illustrated in FIGS. 4*a* and 4*b,* be positioned so that either the front or back edges 144 and 146 is no less than 2 inches (5.1 cm) from its respective front or back edges 44and 46 of the body-side liner 40 while still being symmetrical about the central longitudinal axis A—A. In other words, the pledget 140 can be asymmetrical about the transverse axis B—B.

In other embodiments of the present invention, the breathable absorbent garment 20 includes a single layer absorbent pad 58. The absorbent pad 58 comprises materials adapted to absorb and retain urine, menses, blood or other body excrement. The absorbent pad 58 may comprise various natural or synthetic absorbent materials, such as cellulose fibers, surfactant treated meltblown fibers, wood pulp fibers, regenerated cellulose or cotton fibers, a blend of pulp and other fibers, or the like. One such material is coform material which is composed of a mixture of cellulosic fibers and synthetic polymer fibers. The absorbent pad 58 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. Nos. 4,699,823 issued Oct. 13, 1987, to Kellenberger et at.; and 5,147,343 issued Sep. 15, 1992, to Kellenberger, which are incorporated herein by reference. High-absorbency materials are available from various commercial vendors, such as Dow Chemical Company, Hoechst Celanese Corporation, Stockhausen, Inc., and Allied Colloids, Inc.

One suitable absorbent pad 58 for the breathable absorbent garment 20 is separately illustrated in FIG. 3*a* and comprises an aqueous liquid storage layer 76. The aqueous liquid storage layer 76 comprises an air-laid mixture of about 470 gsm wood pulp fibers and about 305 gsm high-absorbency materials that is sandwiched or wrapped between 19 gsm cellulose tissues (wrap layers 80). The aqueous liquid storage layer 76 is desirably embossed using a matched male/male embossing roll. The typical absorbent pad 58 is hourglass shaped with a length of between about 17 inches (430 mm) and about 25 inches (635 mm) and a width of between about 2.5 inches (64mm) and about 6 inches (152 mm). The absorbent pad 58 desirably has a thickness dimension of less than about 20 mm, particularly less than about 10 mm.

The absorbent pad 58 can comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers. Absorbent pad 58 can comprise only coform, a combination of superabsorbent materials and coform, coform with other absorbent or non-absorbent materials including an acquisition/distribution layer, or any combination thereof.

The coform material may comprise an airlaid blend of cellulosic wood fibers and meltblown polyolefin fibers, such as polyethylene or polypropylene fibers, or may comprise an air-formed batt of cellulosic fibers (i.e., wood pulp fluff). Optionally, the absorbent pad 58 may be treated with a surfactant to aid in aqueous liquid acquisition when in a dry environment. In particular embodiments of the invention, the absorbent pad 58 has a bulk thickness of not more than about 40 mm when dry. The hydrophilic fibers and polymer strands may be provided in a fiber-to-polymer ratio which is greater than 20:80, for example between about 60:40 and about 98:2 and, desirably between about 80:20 and about 90:10. In coform material containing super absorbent materials, the fiber/high absorbency material ratio is between about 90:10 to about 50:50, and desirably between about 60:40 to about 65:35. High absorbency materials are discussed below.

Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof.

The hydrogel polymers are desirably sufficiently cross-linked to render the materials substantially water-insoluble. Cross-linking may, for example, be by irradiation or by covalent, ionic, van der Waals or hydrogen bonding. Suitable materials are available from various commercial vendors, such as Dow Chemical Company, Hoechst-Celanese Corporation, Stockhausen, Inc., and Allied-Colloid. Typically, the high-absorbency material is capable of absorbing at least about 15 times its weight in water, and desirably is capable of absorbing more than about 25 times its weight in water.

The high-absorbency material can be distributed or otherwise incorporated into the absorbent pad 58 employing various techniques. For example, the high-absorbency material can be substantially uniformly distributed among the fibers comprising the absorbent pad 58. The materials can also be non-uniformly distributed within the absorbent pad 58 fibers to form a generally continuous gradient with either an increasing or decreasing concentration of high-absorbency material, as determined by observing the concentration moving inward from the backing member 22. Alternatively, the high-absorbency material can comprise a discrete layer separate from the fibrous material of the absorbent pad 58, or can comprise a discrete layer integral with the absorbent pad 58.

The absorbent pad 58 may also include a wrap layer 80 to help maintain the integrity of the fibrous core. (See FIG. 3*a*.) This wrap layer 80 may comprise a cellulosic tissue or spunbond, meltblown or bonded-carded web material composed of synthetic polymer filaments, such as polypropylene, polyethylene, polyesters or the like or natural polymer filaments such as rayon or cotton.

The absorbent pad 58 should have an aqueous liquid capacity great enough to absorb discharges from about 10 grams to about 1000 grams. The absorbent pad 58 should preferably have a capacity (described below) and a thickness preferably less than about 25 mm, thus providing a non-bulky and flexible fit. The capacity of the absorbent pad 58 should have a total capacity of about 200 grams to about 1300 grams. Preferably, the absorbent pad 58 should have a total capacity of at least about 300 grams to about 1200 grams. More preferably, the total capacity of the absorbent pad 58 should be from about 400 grams to about 800 grams.

The total capacity of the absorbent pad 58 is determined using the absorbent pad 58 of the absorbent garment 20, the body-side liner 40, the backing member 22, and the outer member 38. The saturated retention capacity is a measure of the total absorbent capacity of an breathable absorbent garment 20, in this case an undergarment. The saturated retention capacity is determined as follows. The breathable absorbent garment 20 to be tested, having a moisture content of less than about 7 weight percent, is then weighed and submerged in an excess quantity of the room temperature (about 230° C.) saline solution described below. The material is allowed to remain submerged for 20 minutes. After 20 minutes the breathable absorbent garment 20 is removed from the saline solution and placed on a Teflon™ coated fiberglass screen having 0.25 inch openings (commercially available from Taconic Plastics Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The breathable absorbent garment 20 is weighed. The amount of aqueous liquid retained by the material being tested is determined by subtracting the dry weight of the breathable absorbent garment 20 from the wet weight of the breathable absorbent garment 20 (after application of the vacuum) and is reported as the saturated retention capacity in grams of aqueous liquid retained.

The saline solution is an aqueous solution of about 0.9 percent sodium chloride by weight. A suitable product is S/P™ Certified Blood Saline commercially available from Baxter Diagnostics in McGaw Park, Ill.

The absorbent pad 58 can be made from a blend of fibers comprising about 15 to about 30 weight percent polypropylene fibers and about 85 to about 60 weight percent wood pulp fluff fibers and having a basis weight of 80 to about 250 gsm. The absorbent pad 58 may be formed on a tissue or a spunbonded carrier sheet, or may be formed without a carrier sheet. It is contemplated that the absorbent pad 58 can also be made from a blend of fibers comprising between about 10 weight percent and about 90 weight percent polypropylene or polyethlene fibers and between about 90 weight percent and about 10 weight percent wood pulp fluff fibers. The absorbent pad 58 could also be made from 100 weight percent wood pulp fluff fiber. The basis weight can range between about 80 gsm and about 1000 gsm. The absorbent pad 58 can also be a batt of meltblown fibers such as polypropylene, polyethylene, polyester and the like, and may also be a bonded carded web of synthetic or natural fibers, a composite of meltblown fibers of polypropylene, polyethylene, and polyester mixed with a cellulosic material, or any other suitable absorbent material.

The absorbent pad 58 provides the feature of being able to transport aqueous liquid in what can be characterized as in an x- and y direction and in a z-direction. The transport of aqueous liquid in the z direction is movement of a wicking nature where the aqueous liquid moves away from the body of the wearer. The transport of aqueous liquid in the x-direction and y-direction is movement and/or wicking of aqueous liquid along the length and width of the absorbent layer. As can be appreciated, the movement of aqueous liquid both away from the wearer and along the length and width of the absorbent layer results in an increase in the utilization of the area of the absorbent layer since the aqueous liquid moves towards the distal ends of the absorbent layer, and the result is an improvement of the absorption characteristics of the absorbent layer.

Figure 2:
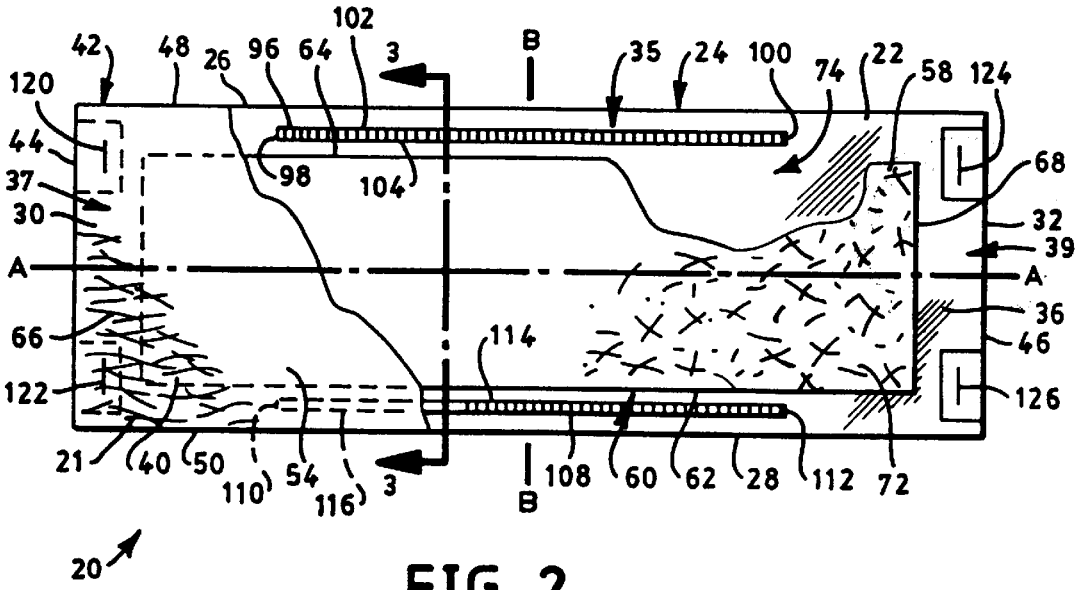
FIG. 2 is a plan view of the specific embodiment of FIG. 1 in an extended condition with the liquid pervious liner facing the viewer, and a portion of the liquid pervious liner and a portion of the absorbent pad removed.

As illustrated in FIGS. 2 and 4*b,* the absorbent pad 58 has a width that is measured between the side edges 62 and 64 thereof. The absorbent pad 58 has a length that is measured between the front end and the back end edges 66 and 68 thereof. The width and length of the absorbent pad 58 are each less than the corresponding width and length of the container 74 comprised of the backing member 22 and the aqueous liquid pervious body-side liner 40. The width of container 74 is measured between the side edges 26 and 28 thereof, and the length of the container 74 is measured between the front and back edges 30 and 32.

The width of the crotch region 35 between the leg elastics 96 and 108 should be wide enough to accommodate the absorbent pad 58 between the side edges 26 and 28 of the absorbent garment 20 without having the absorbent pad 58 obstruct the leg elastics 96 and 108. This allows the leg elastics 96 and 108 to contract and draw up the sides of the crotch region 35 creating a bucket with walls of the body-side liner 40 and backing member 22 to keep bodily exudates from leaking out of the absorbent garment 20 and to accommodate more sizes of individuals.

The width of the crotch region 35 should not be so wide as to seem bulky or uncomfortable, but a suitable width is at least about 2.5 inches (64 mm) between the leg elastics 96 and 108. The width is advantageously ranges from about 2.5 inches (64 mm) to about 14.0 inches (356 mm). Typically the width of the crotch region 35 between the leg elastics 96 and 108 ranges from about 3.5 inches (89 mm) to about 8 inches (203 mm).

The crotch region 35 is at least about 0.25 inch (6 mm) wider than the width of the absorbent pad 58. The crotch region 35 is from about 0.25 inch (6 mm) to about 4 inches (102 mm) wider than the absorbent pad 58. Typically the crotch region 35 is from about 0.5 inch (13 mm) to about 3 inches (76 mm) wider than the absorbent pad 58 and more typically from about 0.5 inch (13 mm) to about 2 inches (51 mm) wider. Preferably, each of the leg elastics 96 and 108 are from about 0.2 inch (5 mm) to about 0.8 inch (20 mm) wide. More preferably, the width of each leg elastics 96 and 108 is from about 0.2 inch (5 mm) to about 0.4 (10 mm). The overall width of the crotch region 35 includes the width between the leg elastics 96 and 108, the width of the leg elastics 96 and 108 and the material (at least including the outer member 38, the backing member 22, and the body-side liner 40) between the leg elastics 96 and 108 and the side edges 26 and 28 of the breathable absorbent garment 20.

Preferably, the material (at least including the outer member 38, the backing member 22, and the body-side liner 40) on the longitudinal edges outside the leg elastics 96 and 108 is less than about 0.5 inch (13 mm). More preferably, the material is less than about 0.125 inch (3 mm).

The overall length of the absorbent pad 58 should be adequate to help prevent aqueous liquid strike through when sleeping or sitting. This overall length is at least about 12 inches (305 mm) thus extending beyond the crotch region 35 along the longitudinal centerline A—A of the breathable absorbent garment 20. Alternatively, the length should be in the range of about 12 inches (305 mm)to about 30 inches (762 mm), more typically ranging from about 15 inches (381 mm) to about 23 inches (584 mm). A common range is from about 15 inches (381 mm) to about 21 inches (533 mm) in length, more typically ranging from about 17 inches (432 cm) to about 20 inches (508 mm).

The width of the absorbent pad 58 extending beyond the crotch region 35 should be at least as wide as the width of the crotch region 35. The width of the absorbent pad 58 could be narrowed beyond the crotch region 35 but may compromise the leakage containment. In some cases, the width of the absorbent pad 58 is widened beyond the crotch region 35. The width of the absorbent pad 58 extending beyond the crotch region 35 is from about 2.5 inches (64 mm) to about 12 inches (305 mm), alternatively from about 4.0 inches (102 mm) to about 10 inches (254 mm). A common range is from about 7 inches (178 mm) to about 9 inches (229 mm).

The present invention contemplates various shapes of the absorbent pad 58. One preferred composite has a non-rectangular shape such as an hourglass or I-beamed shaped absorbent pad 58 which provide extensive coverage in the seat of the finished breathable absorbent garment 20. Another preferred absorbent pad 58 embodiment is rectangular in shape with rounded ends. The essentially rectangular-shaped absorbent pad 58 (i.e. an hourglass shape) is more preferred since it can be squared off at the ends to provide a smoother appearance in the back of the breathable absorbent garment 20 while providing a more comfortable body-contouring fit.

More specifically, the width of the absorbent pad 58 is between about 40 percent and about 90 percent of the width of the container 74 comprised of the impervious backing member 22 and pervious body-side liner 40. The length of the absorbent pad 58 is between about 30 percent and 100 percent of the length of the container 74 comprised of the impervious backing member 22 and the pervious body-side liner 40. More typically, the length of the absorbent pad 58 is between about 40 percent and about 90 percent of the length of the container 74, most typically between about 50 percent and 70 percent of the length of the container 74.

In the specific embodiment, the absorbent pad 58 has a length equal to about 19 inches (48.3 cm), and a width equal to about 4.5 inches (11.4 cm). The width of the absorbent pad can vary, but is typically between about 2.5 inches (6.4 cm) and about 5 inches (12.7 cm) narrower than the width of the impervious backing member 22.

The absorbent pad 58 is typically positioned so as to be symmetrical about the central longitudinal axis A—A of the breathable absorbent garment 20. It need not be symmetrical about the central transverse axis B—B of the breathable absorbent garment 20. In other words, the side edges 62 and 64 of the absorbent pad 58 are equi-distant from side edges 48 and 50 of the aqueous liquid pervious body-side liner 40, respectively. The front end and back end edges 66 and 68 respectively of the absorbent pad 58 are not necessarily equi-distant from the front and back edges 44 and 46 of the aqueous liquid pervious body-side liner 40, respectively. The absorbent pad 58 is disposed in the front waist region 37 and the crotch region 35. The leg elastics 96 and 108 effectively seal between the body of the wearer and the breathable absorbent garment 20 so as to provide good containment properties in the crotch region 35.

The leg elastic 96 has a front edge 98, a back edge 100, an exterior side edge 102, and an interior side edge 104. The leg elastic 96 is affixed adjacent the front edge 48 of the aqueous liquid pervious body-side liner 40 so as to be spaced inwardly therefrom. The leg elastic 96 is positioned so that the front edge 98 and the back edge 100 are equi-distant from their respective front and back edges 44 and 46 of the aqueous liquid pervious body-side liner 40. However, the leg elastic 96 can be positioned other than in an equi-distant arrangement relative to their front and back edges 98 and 100 and the front and back edges 44 and 46 of the aqueous liquid pervious body-side liner 40.

The second leg elastic 108 has a front edge 110, a back edge 112, an interior side edge 114, and an exterior side edge 116. The leg elastic 108 is affixed to the aqueous liquid pervious body-side liner 40 so as to be adjacent to the side edge 50 thereof, and is spaced inwardly of the side edge 50. The leg elastic 108 is positioned so that its front edge 110 and back edge 112 are spaced equi-distant from their respective front and back edges 44 and 46 of the aqueous liquid pervious body-side liner 40. The leg elastic 108 can also be positioned other than in an equidistant arrangement.

While the leg elastics 96, and 108 can be designed to closely follow the edge of the absorbent pad 58 outside of the crotch region 35, moving the leg elastics 96 and 108 away from the absorbent pad 58, the absorbent pad 58 interfers less with the function of the leg elastics 96 and 108, providing better gasketing around the legs of the wearer. In addition, as absorbent pad 58 swells as it absorbs bodily discharges, the leg elastics 96 and 108 so positioned are better able to remain in contact with and conformed to the wearer's body. Such a placement of the leg elastics 96 and 108 is especially beneficial in garment 20 having leg cutouts, as fit protection, and comfort of the garment 20 are improved.

In a preferred embodiment, leg elastics 96 and 108, are attached to the breathable absorbent garment 20 sandwiched between the backing member 22 and the body-side liner 40, in generally a stretched state by means known in the art, including ultrasonic bonding, heat/pressure bonding or adhesively bonding. Materials suitable for the elastics include a wide variety including but not limited to elastic strands, yarn rubber, flat rubber, elastic tape, film-type rubber, polyurethane and elastomeric, tape-like elastomeric or foam polyurethane or formed elastic or non-elastic scrim. Suitable material is sold under the name LYCRA® XA by the DuPont Company located in Wilmington, Del. Each elastic may be unitary, multi-part or composite in construction before integrating into the breathable absorbent garment 20.

In an alternative embodiment, leg elastics 96 and 108, are attached to the breathable absorbent garment 20 sandwiched between the outer member 38 and the backing member 22 in generally a stretched state by means known in the art, such as ultrasonic bonding, heat/pressure bonding or adhesively bonding.

The leg elastics 96 and 108 are from about 0.0625 inch (1.6 mm) to about 1 inch (25 mm) wide, more typically from about 0.25 inch (6 mm) to about 1 inch (25 mm), and most typically from about 0.25 inch (6 mm) to about 0.75 inch (18 mm) such as 0.5 inch (13 mm). The leg elastic 96 and 108 is applied under an elongation of from about 100% to about 350%, more typically under an elongation of from about 150% to about 300%, and most typically under an elongation of from about 225% to about 275%.

The leg elastics 96 and 108 may comprise threads, strands, ribbons, bands, film, elastic nonwovens, or composite. The threads, strands, ribbons, or bands may be multiple and may be applied as a composite. The number of pieces of elastic material comprising the leg elastic 96 and 108 ranges from about 1 to about 6, more typically from about 2 to about 5, and most typically from about 3 to about 4. Preferably, when the leg elastics 96 and 108 are threads, 1 to 6 threads are used as the leg elastics 96 and 108, and the threads are spaced from about 0.0625 inch (1.6 mm) to about 0.5 inches (13 mm), more preferably from about 0.0625 inch (1.6 mm) to about 0.25 inch (6 mm), and most preferably about 0.083 inch (2 mm) apart.

The threads may be made of any suitable elastomeric material. One suitable material is spandex such as LYCRA® threads available from DuPont located in Wilmington, Del. Suitable leg elastics 96 and 108 include threads having a decitex (g/10000m) of from about 470 to about 1200, more typically from about 620 to about 1000, and most typically from about 740 to about 940 for leg elastics 96 and 108 comprising from about 3 to about 6 threads. Adhesive 118, typically applied in a meltblown or swirl pattern using currently known technology, is used to bond the leg elastics 96 and 108 to the outer member 38, the body-side liner 40, or the backing member 22. Preferably the adhesive 118 is applied only to the leg elastics 96 and 108. A suitable adhesive includes, for example, Findley H2096 hot melt adhesive which is available from Ato Findley Adhesives located in Milwaukee, Wis.

In one embodiment, to provide a snug fit around the legs of the wearer and to draw up the sides of the crotch region 35 to form a cradle structure around the absorbent pad 58, the leg elastics 96 and 108 are applied to the backing member 22 or the body-side liner 40 under an elongation of about 200% to about 250%. The leg elastics 96 and 108 are sandwiched between the backing member 22 and the body-side liner 40 under an elongation more preferably of about 200%.

In another embodiment providing a snug fit around the legs of the wearer and drawing the sides of the crotch region 35 up to form a cradle structure around the absorbent pad 58, the leg elastics 96 and 108 are applied to the outer member 38 or the backing member 22 under an elongation of about 200% to about 250%. The leg elastics 96 and 108 are sandwiched between the outer member 38 and the backing member 22, under an elongation more preferably of about 200%.

In the specific embodiment, the leg elastics 96 and 108 are made of urethane. However, it is contemplated that the leg elastics 96 and 108 can be made of natural rubber or other synthetic elastic material.

When stretched for adherence to the garment, the leg elastics 96 and 108 each have a length of about 14 inches (35.6 cm) and a width of about 0.42 inches (1.06 cm). When the leg elastics relax, they each are of a length equal to about 16.5 cm and a width of about 1.27 cm.

A pair of slits 120 and 122, such as button holes, are contained in the container 74 comprised of the aqueous liquid pervious body-side liner 40 and the aqueous liquid impervious backing member 22 adjacent the front edge 30 of the breathable absorbent garment 20. Another pair of slits 124 and 126, such as button holes, are contained in the container 74 comprised of the aqueous liquid pervious body-side liner 40 and aqueous liquid impervious backing member 22 adjacent the back edge 32 of the breathable absorbent garment 20. A strap 130, having retainers 132 and 134, such as buttons, each at opposite ends, extends between the slits 120 and 124. Another strap 136, having retainers 138 and 140, such as buttons, each at opposite ends, extends between the slits 122 and 126. This support system is described in the U.S. Pat. No. 4,315,508 issued Feb. 16, 1982, to Bolick, which is incorporated herein by reference.

Still, other means for securing the garment around the individual includes mechanical type fasteners. These include snaps, buckles, clasps, hooks and loops, end extensions, tabs, adhesive tapes, and the like which are designed or adapted to interlock or engage some type of a complimentary device or the outer cover of the garment. In addition, elasticized fasteners are also used in assuring better fit of such garments. Other absorbent garments 20 may include fully encircling or pre-fastened waist bands.

Figure 5:
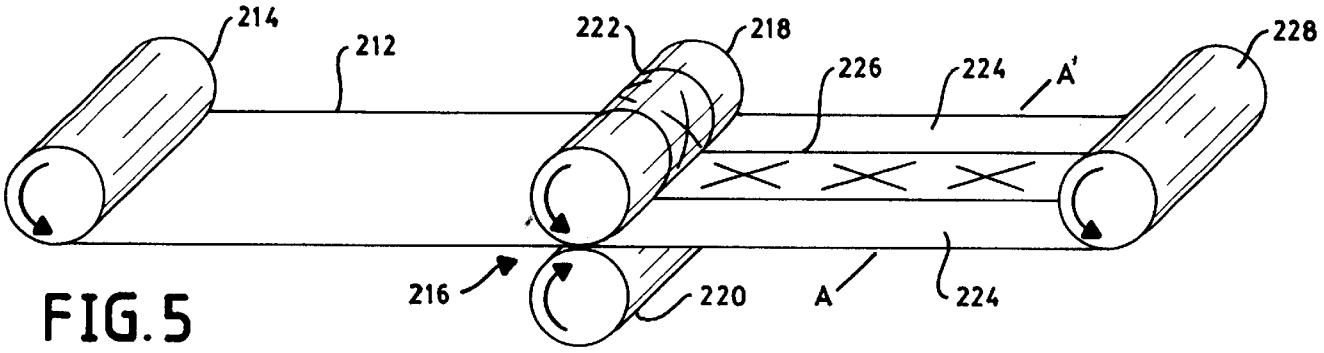
FIG. 5 is a schematic representation of an exemplary nip roll assembly suitable for use in practicing the present invention and a zone treated film made therefrom.

A breathable microporous film can be treated, in accord with the present invention, to create a breathable film backing member 22 having regions of varied breathability. In reference to FIG. 5, microporous film 212 is unwound from supply roll 214 and fed into nip 216 created by first and second nip rolls 218 and 220. The first nip roll 218 can have a patterned surface such as raised surface 222 whereby the film entering nip 216 adjacent raised surface 222 experiences compacting pressure. The second nip roll 220 can be a smooth or unpatterned roll. The microporous film 212 is desirably heated and can be heated prior to entering nip 216 or upon entering the roller assembly. Desirably the film is heated by using one or more heated rolls. The pressure and heat applied to the microporous film 212 reduces the size and/or number of pores within the microporous film thereby reducing the breathability of the film in those selected areas. Thus, a breathable microporous film can be made having regions of controlled breathability. Still in reference to FIG. 5, a microporous film is created having first breathable regions 224 and second regions 226 having a breathability or WVTR lower than that of the first breathable regions 224. The treated film can then be wound on a winder roll 228 or further processed and/or converted as desired.

Suitable microporous films for practicing the present invention include breathable microporous films having a WVTR of at least 500 g/m$^2$/24 hours, and more desirably having a WVTR in excess of 1500 g/m$^2$/24 hours, 2500 g/m$^2$/24 hours or 3500 g/m$^2$/24 hours. Desirably, the breathable microporous film substrate has a WVTR between about 2000 g/m$^2$/24 hours and about 7000 g/m$^2$/24 hours. Thin breathable microporous film can be formed by any one of various methods known in the art. Examples of microporous films suitable for use with the present invention include, but are not limited to, those described in the following references U.S. Pat. No. 5,800,758 issued Sep. 1, 1998 to Topolkaraev et al.; U.S. Pat. No. 4,777,073 issued Oct. 11, 1988, to Sheth; and, U.S. Pat. No. 4,867,881 issued Sep. 19, 1989, to Kinzer; the entire contents of the aforesaid references are incorporated herein by reference.

Additional examples of microporous films suitable for use with the present invention include, but are not limited to, those described in the following references: U.S. Pat. No. 4,613,544 issued Sep.23, 1986, to Burleigh; U.S. Pat. No. 4,833,026 issued May 23, 1989,to Kausch; U.S. Pat. No. 4,863,788issued Sep.5, 1989,to Bellairs et al.; U.S. Pat. No. 4,878,974 issued Nov. 7, 1989, to Kagawa; U.S. Pat. No. 4,620,956 issued Nov.4, 1986, to Hamer; U.S. Pat. No. 4,620,955 issued Nov.4, 1986, to Kono et al.; and, U.S. Pat. No. 5,352,513 issued Oct.4, 1994, to Mrozinski et al.; the entire contents of the aforesaid references are incorporated herein by reference.

A preferred breathable microporous film can comprise a stretched-filled film which includes a thermoplastic polymer and filler. These (and other) components can be mixed together, heated and then extruded into a monolayer or multilayer film. The filled film may be made by any one of a variety of film forming processes known in the art such as, for example, by using either cast or blown film equipment. The thermoplastic polymer and filler can be stretched in at least one direction, thereby reducing the film gauge or thickness and creating a network of micropores throughout the film of a size and frequency to achieve the desired level of breathability. Such films, prior to stretching, desirably have a basis weight of less than about 100 g/m$^2$ and even more desirably less than about 60 g/m$^2$. Upon stretching the multilayer film desirably has a basis weight of less than about 60 g/m$^2$ and even more desirably between about 15 and 35 g/m$^2$. Suitable films can also include multilayer films having at least one microporous layer such as, for example, those described in the references cited above.

The microporous films can comprise known film forming polymers which are, by mechanical and/or thermal treatment, permanently deformable. Mechanically deformable polymer films are believed to be suitable for use with the present invention (e.g. soft rubbers). Desirably the microporous film is made from a thermoplastic polymer. Preferred thermoplastic polymers used in the microporous films of the present invention include, but are not limited to, polyolefins including homopolymers, copolymers, terpolymers and blends thereof. Additional film forming polymers suitable for use with the present invention, alone or in combination with other polymers, include ethylene vinyl acetate, ethylene ethyl acrylate, ethylene acrylic acid, ethylene methyl acrylate, ethylene normal butyl acrylate, polyester, polyethylene terephthalate, polyamides (e.g. nylon), ethylene vinyl alcohol, polystyrene, polyurethane, polybutylene, and polybutylene-terephthalate. However, polyolefin polymers are preferred such as, for example, polymers of ethylene and propylene as well as copolymers, terpolymers and blends thereof; examples include, but are not limited to, linear low density polyethylene (LLDPE) and ethylene-propylenecopolymer blends. The microporous films can comprise elastic or inelastic polymers. However, with elastic microporous films sufficient energy, e.g. heat and/or pressure, should be imparted to "set" the treated region of the film.

Once the breathable microporous film has been formed, that is the fine pore network has been created across the film, the microporous film can be treated to impart zoned or controlled regional breathability to the film. The microporous film can be made in-line or made previously and unwound from a supply roll. Selected regions of the microporous film are treated with sufficient energy (e.g. pressure and/or heat) to reduce the number and/or size of pores therein and thereby reduce and/or substantially eliminate the breathability previously imparted to the film in that region. For example, the microporous film can be passed through a pair of patterned nip rollers which apply a predetermined amount of pressure to reduce the pore structure to a desired degree. The degree of pressure applied by the nip rolls will vary with respect to the type of polymer comprising the microporous film, the thickness of the microporous film, the temperature of the film and the level of breathability desired in the zone treated regions.

Desirably one of the nip rolls is patterned so as to have a raised surface. The rollers can have varied patterns to create the zoned breathability in the film as desired. However, small discrete raised projections on the nip roll can create a film with degraded barrier properties and/or strength. Thus, the raised surface of the roller(s) is such that the corresponding treated regions of the film extend at least 3 cm in the CD and MD and more desirably at least 5 cm×5 cm in the CD and MD. Further, the raised surface or can extend at least 10 cm in either the CD or MD direction. In a further aspect of the invention, the treated regions desirably comprise from about 5% to about 90% of the area of the film. In a preferred embodiment of the present invention the treated regions comprise a contiguous area comprising from about 5% to about 75% of the area of the overall film and more desirably comprise from about 15% to about 60% of the area of the film. In a further embodiment, the regions can comprises a plurality of regions of intermediate and low breathability. The regions of low and intermediate breathability desirably form a single contiguous area and which can, in one aspect, be disposed about the central portion of the film. However, the treated regions can comprise several non-contiguous regions.

Figure 7:
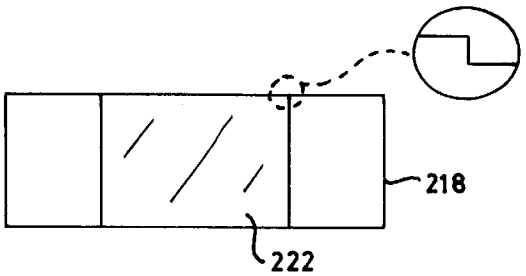
FIG. 7 is a cross-section representation of an exemplary patterned roll suitable for use in practicing the present invention.

In one embodiment of the present invention, the patterned nip roll can have a raised surface which is continuous. As an example, raised surface 222 can extend around the circumference of a roll such as first nip roll 218 shown in FIGS. 5 and 7. First nip roll 218 having raised surface 222 is shown in FIG. 7 with an enlarged view of the raised surface edge. Raised surface 222 can have a squared off edge although it is advantageous to employ a rounded or tapered edge along the raised surface of the nip roll. Each of the nip rolls desirably have a hard surface, such as steel rolls, although other materials are believed suitable with the present invention. As an example, it is believed a rubber coated roll may be advantageous when used in connection with a patterned steel roll. In a further aspect, the patterned roll can have shims along the edge of the patterned roll at the same height of the raised surface to stabilize the rolls and/or improve processing of the film. Desirably the film is of a size and also fed into the nip such that it does not pass under the shims.

The location of the raised surface(s) can be placed upon the patterned nip roll to treat the microporous film in the desired locations. For example, a patterned roll having a continuous raised surface about the center of the roll can be used to create a zoned breathability microporous film, such as shown in reference to FIG. 5, having highly breathable regions 224 adjacent the opposed edges of the film and central region 226 of reduced breathability therebetween. The reduced breathability region 226 can extend continuously in the machine direction of the microporous film. In a further aspect of the invention, when using a continuous raised surface that extends around the entire circumference of a given length of the roll, the nip pressure can be varied in order to further modify the breathability of the corresponding region of the film. For example, the hydraulic pressure on the rollers could be oscillated in order to achieve varied levels of breathability extending in the machine direction.

Figure 8:
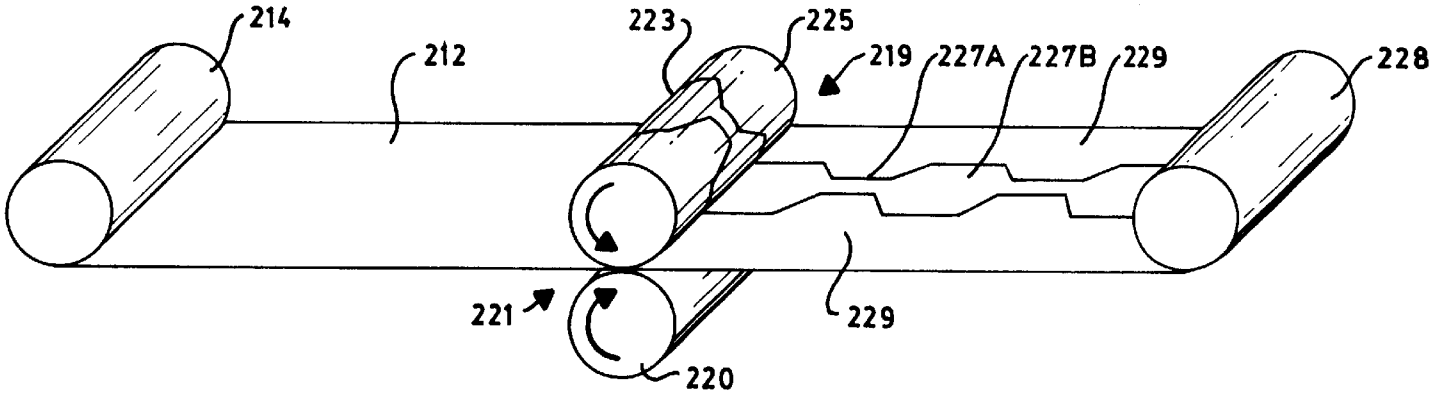
FIG. 8 is a schematic representation of an exemplary nip roll assembly suitable for practicing the present invention and a zone treated film made therefrom.

In a further aspect of the invention, the raised surface or surfaces can be shaped to create correspondingly shaped regional breathability to the microporous film. In reference to FIG. 8, patterned roll 219 can have raised surface 223 and lower surface 225. Microporous film 212 is fed through nip 221 created by rolls 219 and 220 thereby creating a film having first region 229 and second region 227A wherein first region 229 has a higher WVTR than second region 227A. Further, it is believed that continuous region 227 itself will have varied levels of breathability. Narrow sections, second region 227A, will have a lower WVTR than wide sections, third region 227B. It is believed that the pounds per linear inch (typically referred to as pressure/unit area) experienced by microporous film 212 will be greater in the narrower sections thereby effecting a greater decrease in film breathability in those areas.

Figure 9:
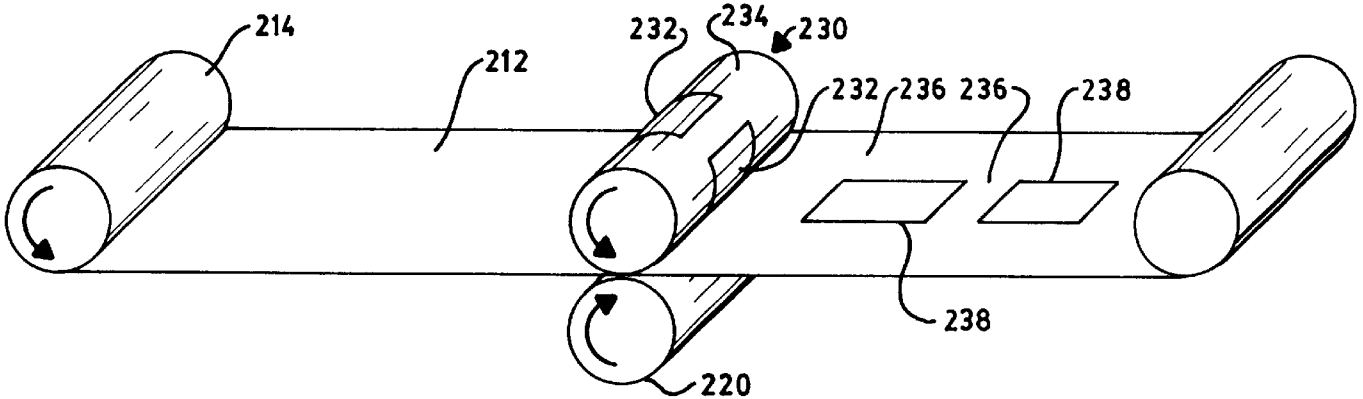
FIG. 9 is a schematic representation of an exemplary nip roll assembly suitable for use in practicing the present invention and a zone treated film made therefrom.

In a further aspect, the raised surface can be discontinuous in the sense that the raised surface extends around only a portion of the rolls circumference. In reference to FIG. 9, patterned roll 230 has raised surface 232 and lower surface 234 wherein raised surface 232 extends around less than the entire periphery of roll 230. Treatment of a microporous film with such a roll will create first region 236 and second region 238 whereby first region 236 has greater breathability than second region 238. Further, second region 238 will be separated by portions of first region 236 in the machine direction.

Figure 10:
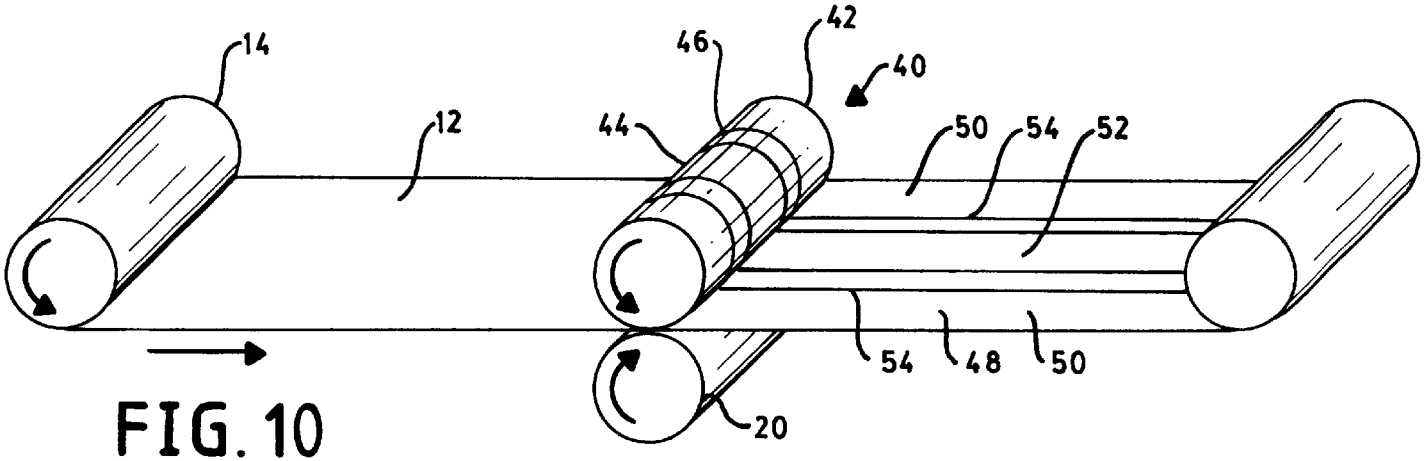
FIG. 10 is a schematic representation of an exemplary nip roll assembly suitable for use in practicing the present invention and a zone treated film made therefrom.
Figure 11:
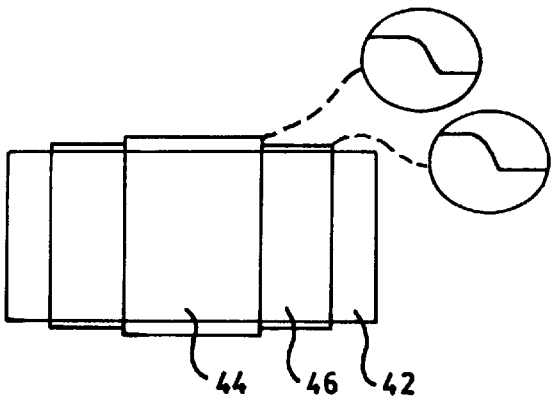
FIG. 11 is a cross-section representation of an exemplary patterned roll suitable for use in practicing the present invention.
Figure 12:
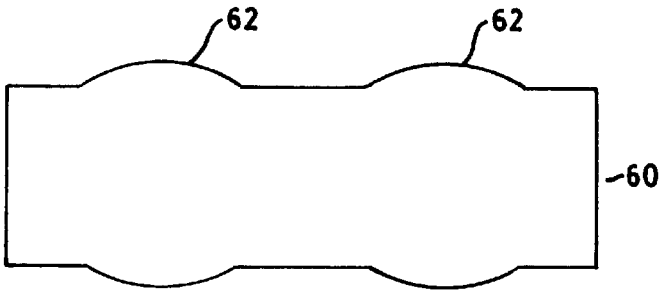
FIG. 12 is a cross-section representation of an exemplary patterned roll suitable for use in practicing the present invention.

As a further example, a patterned roll can have multiple stepped raised surfaces to create a breathability gradient across the CD of the film. In reference to FIGS. 10 and 11, patterned roll 240 has first surface 242, a second surface 244 and a third surface 246 wherein second surface 244 and third surface 246 are raised surfaces relative to first surface 242. Further, third surface 246 can be disposed between first and second surfaces 242 and 244 having an in intermediate height relative to the adjacent surfaces. The resulting zoned breathable film 248 film will have first region 250 of high breathability, second region 252 of low breathability and third region 254 of intermediate breathability. In a further aspect of the invention and in reference to FIG. 12, patterned roll 260 can utilize a crowned or rounded roll, having raised surfaces 262 while having a more regular surface. A film treated in accord with such a patterned roller will have regions of varied breathability with a breathability gradient across the CD of the film as opposed to substantially distinct regions of breathability.

In regard to the height of the raised surfaces of the roll(s), this height will vary with respect to the thickness of the untreated microporous film, the level of breathability desired and the hardness of the nip rolls. Desirably the raised surface of the nip has a height of at least 10 microns and more desirably has a height of between about half the thickness of the untreated film and about 1 mm.

In addition to pressure, additional energy such as thermal energy can be applied to the film. The particular combination of pressure and heat applied to the film will vary with regard the particular polymers and fillers involved and the desired characteristics of the treated films. Generally speaking, at equivalent pressures, films heated to higher temperatures experience a greater decrease in WVTR and/or thickness. Further, it has been found that CD strength is improved by heating the film to a higher degree. Desirably sufficient thermal energy is applied to heat the film to about the polymer softening point and is further desirable that the film not be heated to or above its melting point. However, although use of relatively higher film temperatures are believed suitable for use with the present invention, it is believed that at such temperatures it will be difficult to achieve a controlled level of film breathability. The general relationship between nip pressure, film temperature and impact on film WVTR for thermoplastic polymers is further exemplified in the actual examples set forth below.

Figure 6:
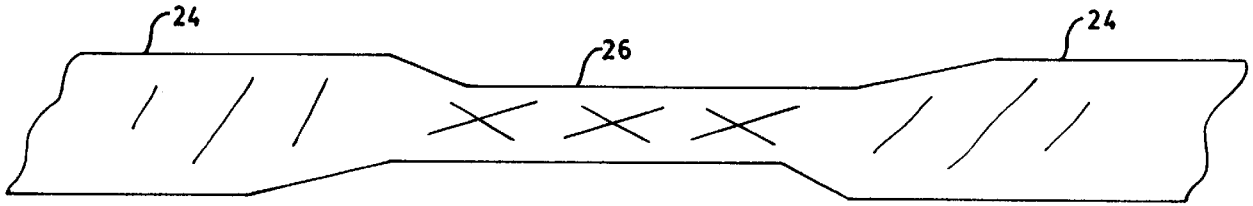
FIG. 6 is a cross-section of a treated microporous film shown in FIG. 5 take at A—A'.
Figure 13:
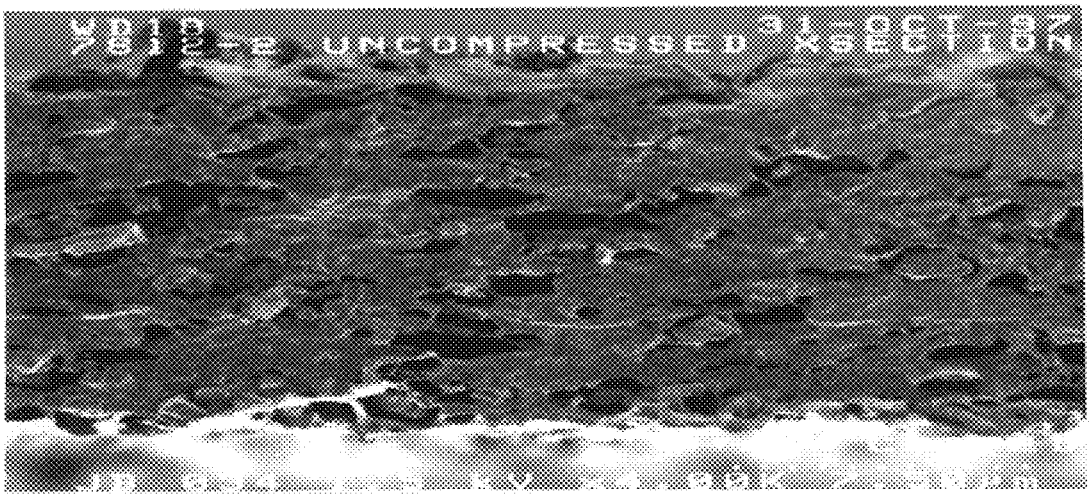
FIG. 13 is a photomicrograph of an untreated region of a microporous breathable film.
Figure 14:
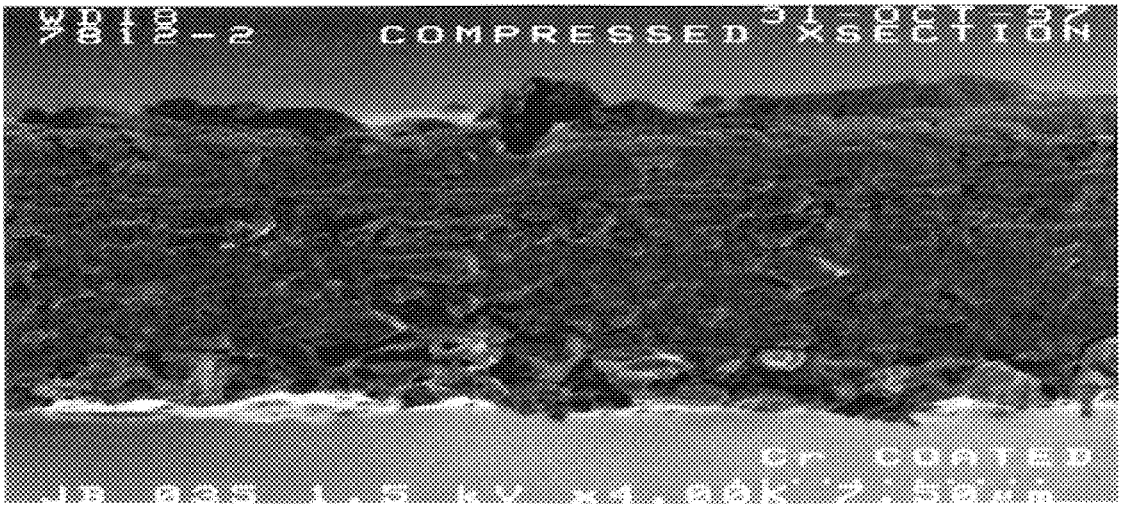
FIG. 14 is a photomicrograph of an treated region of the same microporous breathable film shown in FIG. 13.

The zoned treatment of the microporous film acts to reduce the number and/or size of the pores in the treated regions thereby reducing the WVTR or breathability in those same regions. In reference to FIG. 5 and 6, the zone treated microporous film can have a first substantially uncompressed region 224 which has a higher level of breathability than the second compressed region 226 of the film. The compressed or second region 226 will substantially correspond to those areas of the film to which heat and/or pressure is applied via the raised regions 222 of the patterned nip roll 218. In addition, the treated regions will, despite having a lower WVTR, typically have a thickness which is thinner than the substantially uncompressed regions. Although the relative thickness will vary, the compressed regions typically have a thickness which is less than about 95% of the thickness of the untreated region and in other embodiments can be less than about 90% or even less than about 80% of the thickness of the untreated regions. In this regard it is believed that decrease in film thickness provides a corresponding decrease in WVTR. Further, as a result of the treatment, some retraction may occur changing the film basis weight. FIGS. 13 and 14, respectively, are photomicrographs of a cross-section of a substantially uncompressed region of filled microporous film and a compressed region of the same film. In addition, with stretched-filled microporous films of about 35 g/m$^2$ or less, upon application of sufficient heat and pressure, the compressed regions can become translucent and/or exhibit decreased opacity relative to the substantially uncompressed regions.

In another embodiment of the present invention, a breathable microporous film 412 can be treated, in accord with the present invention, to create a breathable film backing member 22 having regions of varied breathability using adhesives or other coating materials. In reference to FIG. 15*a* and 15*b,* microporous film 412 is unwound from supply roll 414. A meltblown adhesive applicator 416, including but not limited to a Nordson Control Coat CC-200 available from the Nordson Corporation at Norcross, Ga., applies an adhesive layer 418 to the body-side surface 420 of the microporous film 412. The adhesive layer 418 is applied in an open pattern and as such, has minimal effect on the breathability of the microporous film 412. A second adhesive applicator 422, including but not limited to a Nordson EP45 contact type coating head available from the Nordson Corporation at Norcross, Ga., is pulsed to apply an adhesive coat layer 424 on to areas where less breathability is desired. The amount of adhesive applied in the adhesive coat layer 424 depends on the desired reduction in breathability. The adhesive coat layer 424 applied to the microporous film 412 reduces the size or number of pores within microporous film 412 at least partially covers or fills the pores, thereby reducing the breathability of the film in these selected areas. Thus, a breathable microporous film 412 can be made having regions of controlled breathability. As shown in FIG. 16*a* and 16*b,* a microporous film 412 is created having a first breathable regions 426 and second regions 428 having a breathability or WVTR lower than that of the first regions 426. The treated film 412 can then be wound on a winder roll 430 or further processed or converted as desired.

The term "adhesive" or "adhesives" as used herein includes, but is not limited to, any material which will adhere to the microporous film when applied by some coating apparatus, thereby reducing the WVTR of the microporous film where the adhesive has been applied.

The adhesive layer 418 can be applied over the entire body-side surface 420 of the microporous film 412 or the adhesive layer 418 can be applied in the areas only where the adhesive coat layer 424 will not be applied. The adhesive layer 418 is typically a construction adhesive, the adhesive used to attach the various components of product into which the microporous film 412 is incorporated. The adhesive layer 418 preferably is from about 1 gsm to about 7 gsm, more preferably from about 2 gsm to about 5 gsm, and most preferably 3.2 gsm. An example of a construction adhesive is 34-5610 from the National Starch and Chemical Company in Bridgewater, N.J.

In another embodiment of the present invention, a breathable microporous film 412 can be treated, in accord with the present invention, to create a breathable film backing member 22 having regions of varied breathability using adhesives. In reference to FIG. 15*a,* microporous film 412 is unwound from supply roll 414. An adhesive applicator 422, including but not limited to a Nordson EP45 contact type coating head available from the Nordson Corporation at Norcross, Ga., is pulsed to apply an adhesive coat layer 424 on to areas where less breathability is desired. The amount of adhesive applied in the adhesive coat layer 424, as well as the type of adhesive and the type of adhesive application, determines the desired reduction in breathability. The adhesive coat layer 424 applied to the microporous film 412 at least partially covers or fills the pores within the microporous film 412, thereby reducing the size or number of pores within microporous film 412 thereby reducing the breathability of the film in these selected areas. Thus, a breathable microporous 412 can be made having regions of controlled breathability. As shown in FIG. 16*a* and 16*b,* a microporous film 412 is created having a first breathable regions 426 and second regions 428 having a breathability or WVTR lower than that of the first regions 426. The treated film 412 can then be wound on a winder roll 430 or further processed or converted as desired.

While it may be typical to apply the adhesive coat layer 424 to the body-side surface 420 of the microporous film 412, the adhesive coat layer 424 may be applied to the garment-side surface 421 of the microporous film 412.

In certain circumstances, it may be beneficial to leave the portions of the backing member 22 free of the adhesive coat layer 424 where the leg elastics 96 and 108 are positioned as the adhesive coat layer 424 may interfere with the application of the leg elastics 96 and 108 during the construction of the breathable absorbent garment 20.

Suitable microporous films for practicing this embodiment of the present invention include breathable microporous films having a WVTR of at least 500 g /$m^2$/24 hours, and more desirably having a WVTR in excess of 1500 g/$m^2$/24 hours, 2500 g/$m^2$/24 hours or 3500 g/$m^2$/24 hours. Desirably, the breathable microporous film substrate has a WVTR between about 2000 g/$m^2$/24 hours and about 7000 g/$m^2$/24 hours. Thin breathable microporous film can be formed by any one of various methods known in the art. Examples of microporous films suitable for use with the present invention include, but are not limited to, those described in the following references: U.S. Pat. No. 5,800,758 issued Sep. 1, 1998 to Topolkaraev et al.; U.S. Pat. No. 4,777,073 issued Oct.11, 1988, to Sheth; and, U.S. Pat. No. 4,867,881 issued Sep. 19, 1989, to Kinzer; the entire contents of the aforesaid references are incorporated herein by reference.

Additional examples of microporous films suitable for use with the present invention include, but are not limited to, those described in the following references: U.S. Pat. No. 4,613,544 issued Sep. 23, 1986, to Burleigh; U.S. Pat. No. 4,833,026 issued May 23, 1989, to Kausch; U.S. Pat. No. 4,863,788 issued Sep. 5, 1989, to Bellairs et al.; U.S. Pat. No. 4,878,974 issued Nov. 7, 1989, to Kagawa; U.S. Pat. No. 4,620,956 issued Nov.4, 1986, to Hamer; U.S. Pat. No. 4,620,955 issued Nov.4, 1986, to Kono et al.; and, U.S. Pat. No. 5,352,513 issued Oct.4, 1994, to Mrozinski et al.; the entire contents of the aforesaid references are incorporated herein by reference.

A preferred breathable microporous film can comprise a stretched-filled film which includes a thermoplastic polymer and filler. These (and other) components can be mixed together, heated and then extruded into a monolayer or multilayer film. The filled film may be made by any one of a variety of film forming processes known in the art such as, for example, by using either cast or blown film equipment. The thermoplastic polymer and filler can be stretched in at least one direction, thereby reducing the film gauge or thickness and creating a network of micropores throughout the film of a size and frequency to achieve the desired level of breathability. Such films, prior to stretching, desirably have a basis weight of less than about 100 g/$m^2$ and even more desirably less than about 60 g/$m^2$. Upon stretching the multilayer film desirably has a basis weight of less than about 60 g/$m^2$ and even more desirably between about 15 and 35 g/$m^2$. Suitable films can also include multilayer films having at least one microporous layer such as, for example, those described in the references cited above.

The microporous films can comprise known film forming polymers which are, by mechanical and/or thermal treatment, permanently deformable. Mechanically deformable polymer films are believed to be suitable for use with the present invention (e.g. soft rubbers). Desirably the microporous film is made from a thermoplastic polymer. Preferred thermoplastic polymers used in the microporous films of the present invention include, but are not limited to, polyolefins including homopolymers, copolymers, terpolymers and blends thereof. Additional film forming polymers suitable for use with the present invention, alone or in combination with other polymers, include ethylene vinyl acetate, ethylene ethyl acrylate, ethylene acrylic acid, ethylene methyl acrylate, ethylene normal butyl acrylate, polyester, polyethylene terephthalate, polyamides (e.g. nylon), ethylene vinyl alcohol, polystyrene, polyurethane, polybutylene, and polybutylene terephthalate. However, polyolefin polymers are preferred such as, for example, polymers of ethylene and propylene as well as copolymers, terpolymers and blends thereof; examples include, but are not limited to, linear low density polyethylene (LLDPE) and ethylene-propylene copolymer blends. The microporous films can comprise elastic or inelastic polymers. However, with elastic microporous films sufficient energy, e.g. heat and/or pressure, should be imparted to "set" the treated region of the film.

Once the breathable microporous film 412 has been formed, that is the fine pore network has been created across the film, the microporous film 412 can be treated to impart zoned or controlled regional breathability to the film. The microporous film 412 can be made in-line or made previously and unwound from a supply roll. Selected regions of the microporous film are treated with sufficient adhesive to at least partially cover or fill the pores of the film, thereby reducing the number and/or size of pores therein and thereby reduce and/or substantially eliminate the breathability previously imparted to the film in the treated region. The breathability is directly dependent upon the thickness (the amount of adhesive or the percentage of coverage), the type of adhesive used, and the type of adhesive application used in applying the adhesive coat layer 424 to the microporous film 412. The thicker or more uniform the adhesive coat layer 424 applied to the microporous film 412, the more pores of the microporous film 412 will be covered or filled, thereby reducing the breathability of the microporous film 412. In addition, the breathability of the microporous film 412 can be varied by varying a combination of any or all of the following factors: the thickness of the adhesive coat layer 424 (the amount of adhesive or the percentage of coverage), the type of adhesive used in the adhesive coat layer 424, and the type of adhesive application used to apply the adhesive coat layer 424 to the microporous film 412.

The treated regions of the film extend at least 3 cm in the CD and MD and more desirably at least 5 cm×5 cm in the CD and MD. Further, the treated regions of the surface can extend at least 10 cm in either the CD or MD direction. In a further aspect of the invention, the treated regions desirably comprise from about 5% to about 90% of the area of the film. In a preferred embodiment of the present invention the treated regions comprise a contiguous area comprising from about 5% to about 75% of the area of the overall film and more desirably comprise from about 15% to about 60% of the area of the film. In a further embodiment, the regions can comprise a plurality of regions of intermediate and low breathability. The regions of low and intermediate breathability desirably form a single contiguous area and which can, in one aspect, be disposed about the central portion of the film. However, the treated regions can comprise several non-contiguous regions and need not be centered on the breathable backing member 22.

Figure 15A:
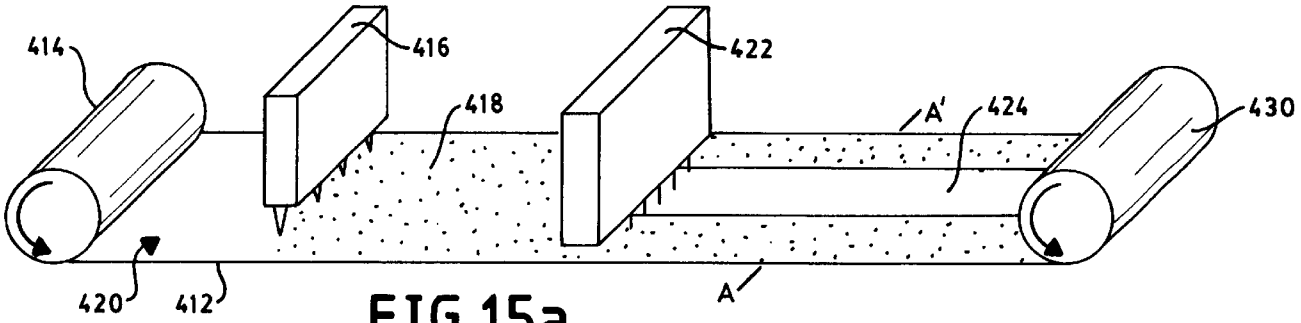
FIG. 15*a* is a schematic representation of an exemplary adhesive applicator assembly suitable for use in practicing the present invention and a zone treated film made therefrom.
Figure 15B:
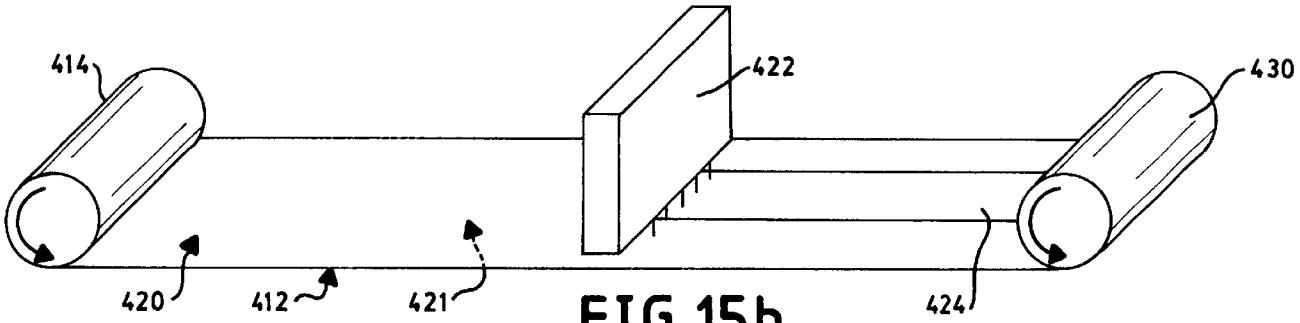
FIG. 15*b* is a schematic representation of an exemplary adhesive applicator assembly suitable for use in practicing the present invention and a zone treated film made therefrom.
Figure 16B:
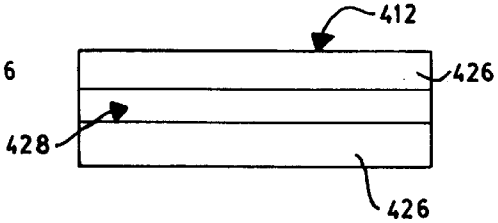
FIG. 16*b* is a plan view of a zone treated microporous film suitable for use in practicing the present invention.
Figure 16A:
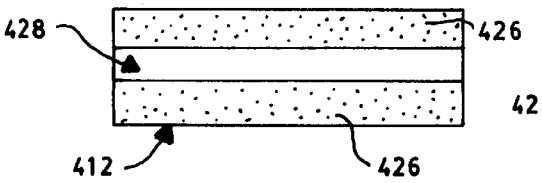
FIG. 16*a* is a plan view of a zone treated microporous film suitable for use in practicing the present invention.
Figure 17A:
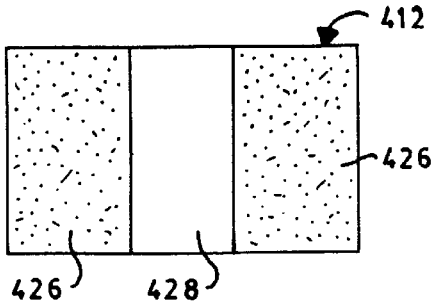
FIG. 17*a* is a plan view of a zone treated microporous film suitable for use in practicing the present invention.
Figure 17B:
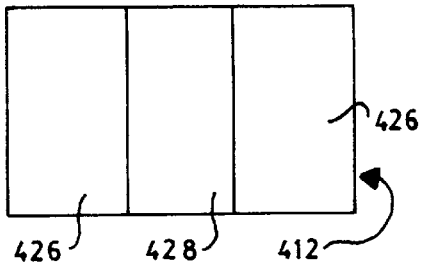
FIG. 17*b* is a plan view of a zone treated microporous film suitable for use in practicing the present invention.

In one embodiment of the present invention, the adhesive coat layer 424 can be applied in a continuous pattern as seen in second regions 426 in FIG. 15*a*. The adhesive coat layer 424 can also be applied such that a continuous second region 428 is disposed in the center of the microporous film 412, creating a zoned breathability microporous film 412, such as shown in FIG. 17*a* and 17*b*, having highly breathable regions 426 adjacent the opposed edges of the film and a central second region 428 of reduced breathability therebetween. The reduced breathability region 428 can extend continuously in the machine direction of the microporous film. In a further aspect of the invention, the thickness (amount of adhesive or percentage of coverage) of the adhesive coat layer 424 can be varied in order to further modify the breathability of the corresponding region of the film. Varying the thickness of the adhesive coat layer 424 results in varied levels of breathability extending in the machine direction.

Varying the thickness (including amount or percentage of coverage by the adhesive coat layer 424) is one method of controlling the breathability of the microporous film 412. Other methods include changing the method of application of the adhesive coat layer 424. For example, a meltblown application of 3.2 gsm of adhesive onto the microporous film 412 has very little effect on the WVTR of the microporous film 412. However, the slot coating application of 3.2 gsm of adhesive onto the microporous film 412 has a marked effect on the WVTR of the microporous film 412.

Figure 19A:
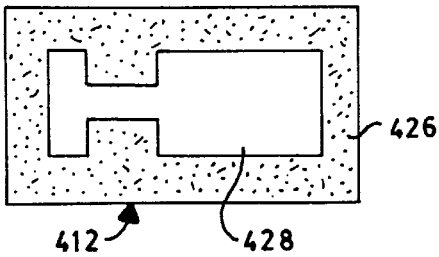
FIG. 19*a* is a plan view of a zone treated microporous film suitable for use in practicing the present invention.
Figure 19B:
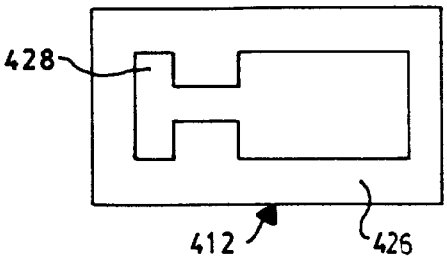
FIG. 19*b* is a plan view of a zone treated microporous film suitable for use in practicing the present invention.

In a further aspect of the invention, the adhesive coat layer 424 can be applied in so as to create shaped regional breathability to the microporous film. In reference to FIG. 19*a* and 19*b,* the adhesive coat layer 424 can be applied in different thicknesses (or types of adhesives applied or the type of adhesive application as discussed above) in second regions 428 having different WVTRs. Thus, the microporous film 412 is thereby creating having first region 426 and second region 428 wherein first region 426 has a higher WVTR than second region 428. The narrow sections, second region 428, can be treated to have a higher or lower WVTR than wide sections, third region 429.

Figure 18A:
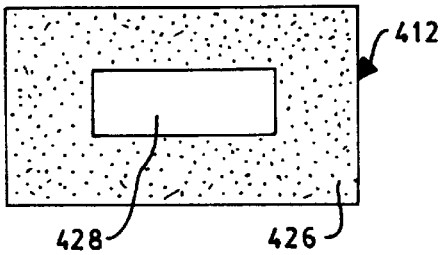
FIG. 18*a* is a plan view of a zone treated microporous film suitable for use in practicing the present invention.
Figure 18B:
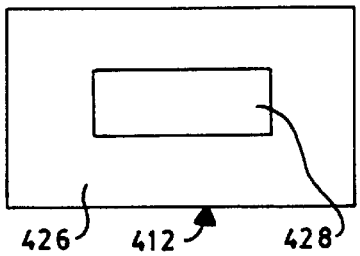
FIG. 18*b* is a plan view of a zone treated microporous film suitable for use in practicing the present invention.

In a further aspect, the application of the adhesive coat layer 424 can be discontinuous in the sense that the adhesive is applied in a broken pattern as shown in FIGS. 18*a,* 18*b,* and 20. The treatment of a microporous film 412 as such create first region 426 and second region 428 whereby first region 426 has greater breathability than second region 428. Further, second region 428 will be separated by portions of first region 426 in the machine direction.

As a further example, the adhesive coat layer 424 can be applied in a manner to create a breathability gradient across the CD of the film. In reference to FIGS. 20 and 21, one such configuration can result in a zoned breathable film 412 having a first region 426 of high breathability, second region 428 of low breathability and third region 429 of intermediate breathability.

As a further example, the adhesive coat layer 424 can be applied in a mmaner to create a breathability gradient across the CD of the film 412. In reference to FIG. 21, one such configuration can result in a zoned breathable film 412 having a first region 426 of high breathability, a second region 428 of low breathability and a third region 429 of intermediate breathability. The adhesive coat layer 424 applied in the second region 428 is thicker (an increased amount or a higher percentage of coverage of the adhesive layer 424) than the adhesive coat layer 424 in the CD of the microporous film 412, a breathability gradient having regions of varied breathability across the CD of the microporous film 412 is created as opposed to substantially distinct regions of breathability.

As a further example, the adhesive coat layer 424 can be applied in a manner to create a breathability gradient across the CD of the film. In reference to FIG. 21, one such configuration can result in a zoned breathable film 412 having a first region 426 of high breathability, second region 428 of low breathability and third region 429 of intermediate breathability. The adhesive coat layer 424 applied in the second region 428 is of a different type of adhesive for use in the adhesive coat layer 424 applied in the third region 429, resulting in a breathability gradient. By varying the type of the adhesive coat layer 424 in the CD of the microporous film 412 a breathability gradient having regions of varied breathability across the CD of the microporous film 412 is created as opposed to substantially distinct regions of breathability.

Figure 21:
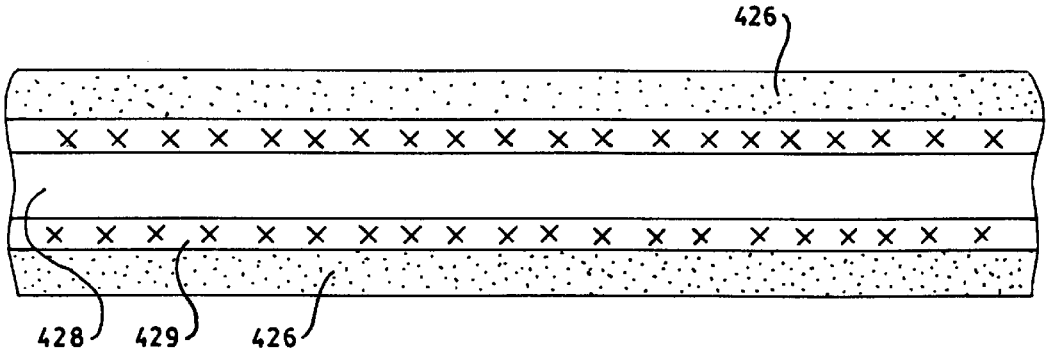
FIG. 21 is a schematic representation of an adhesive application pattern suitable for use in practicing the present invention.

As a further example, the adhesive coat layer 424 can be applied in a manner to create a breathability gradient across the CD of the film. in reference to FIG. 21, one such configuration can result in a zoned breathable film 412 having a first region 426 of high breathability, second region 428 of low breathability and third region 429 of intermediate breathability. The adhesive coat layer 424 applied in the second region 428 under a different method of adhesive application of the adhesive coat layer 424 than used to apply the adhesive coat layer 424 to the third region 429, resulting in a breathability gradient. By varying the type of adhesive application of the adhesive coat layer 424 in the CD of the microporous film 412, a breathability gradient having regions of varied breathability across the CD of the microporous film 412 is created as opposed to substantially distinct regions of breathability.

The zoned treatment of the microporous film 412 acts to at least partially cover or fill the pores of the microporous film 412, thereby reducing the number or size of the pores in the treated regions thereby reducing the WVTR or breathability in those same regions. In reference to FIGS. 16*a* and 16*b,* the zone treated microporous film can have a first substantially untreated region 426 which has a higher level of breathability than the second adhesively treated region 428 of the microporous film. It is understood that the phrase "substantially untreated region" refers herein to regions that may have undergone a treatment, however the treatment had little or no effect on the WVTR of the microporous film 412. The second region 428 will substantially correspond to those areas of the microporous film to which an adhesive coat layer 424 has been applied.

In a further aspect of the invention, the zoned breathability microporous film 412 can be joined with one or more additional layers. Alternatively, additional layers can be attached to the microporous film prior to zone treating the film. Desirably the microporous film is attached to a pliable support layer capable of being laminated to the film such as, for example, a pliable fibrous, film and/or foam material. Exemplary fibrous layers include, but are not limited to, nonwoven webs, multilayer nonwoven laminates, scrims, woven fabrics, slit films and/or other like materials. Desirably the support fabric comprises one or more layers of spunbonded and/or meltblown fiber webs including, but not limited to, monocomponent spunbond fiber webs, multicomponent spunbond fiber webs, split fiber webs, multilayer nonwoven laminates, bonded carded webs and the like. Generally, the composition of the fibrous layer may be selected to achieve the desired properties, i.e. hand, aesthetics, tensile strength, cost, abrasion resistance, hook engagement, etc. Further, the fibrous layer can also be treated such as, for example, by embossing, hydroentangling, mechanically softening, printing or treated in another manner in order to achieve additional desired characteristics. In one embodiment the outer layer may comprise about a 10 $g/m^2$ to about 68 $g/m^2$ web of spunbonded polyolefin fibers and even more desirably a 10 $g/m^2$ to about 34 $g/m^2$ web of such fibers. The fibrous layer can be attached or laminated to the microporous film by adhesive bonding, thermal bonding, ultrasonic bonding or other means known in the art. In one aspect of the invention the microporous film and fibrous layer are bonding with an adhesive sprayed via a standard meltblown die to either the nonwoven fabric and/or film. In a further aspect of the invention, the fibrous layer and microporous film can be laminated via thermal point bonding.

The microporous films of the present invention having controlled regional breathability can be used with a wide variety of products or as components of products such as, for example, in personal care articles, infection control products, protective covers, garments and the like. As a particular example, a microporous film similar to that shown in to FIGS. 16*a,* 16*b,* 17*a,* 17*b,* 18*a,* 18*b,* 19*a,* 19*b,* and 20 can be readily converted and incorporated within a breathable barrier of a diaper or incontinence garment whereby the regions of reduced breathability of the microporous film extend along the central portion or crotch of the diaper and generally cover these regions of the absorbent pad 58 likely to contain large amounts of aqueous liquid waste when the absorbent garments 20 are used. The regions more or less coextensive with the absorbent pad 58 are typically of lower breathability. By covering the absorbent pad 58 with areas of lower breathability, the chance of the outside of the absorbent garment 20 feeling wet is minimized. (See FIGS. 22, 23, 24, and 25.).

Figure 20:
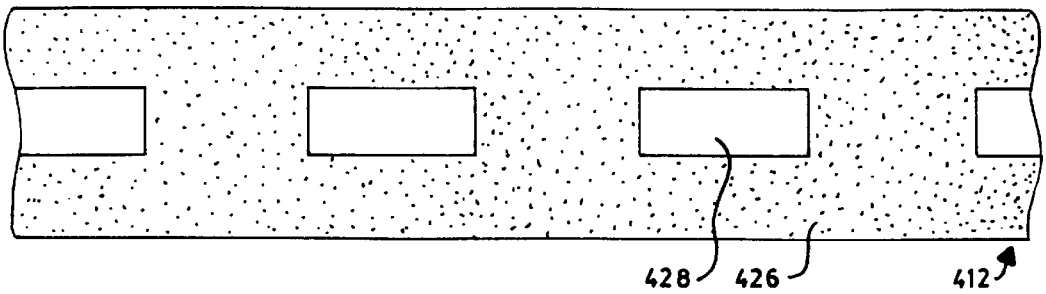
FIG. 20 is a schematic representation of an adhesive application pattern suitable for use n practicing the present invention.
Figure 22:
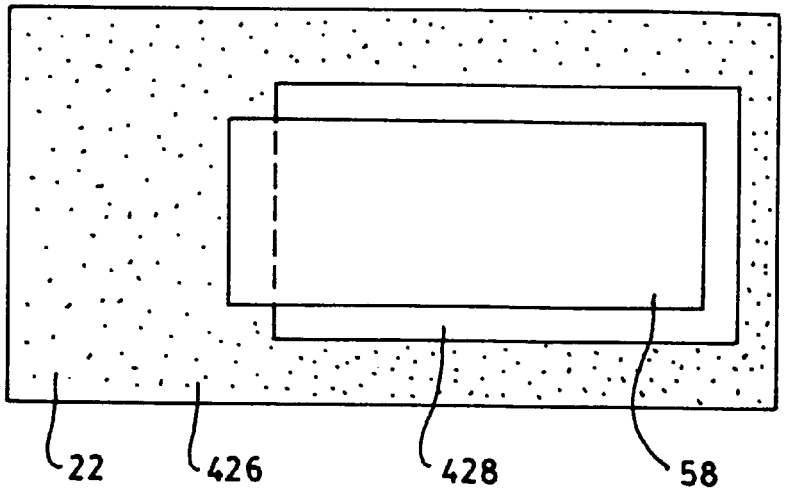
FIG. 22 is a plan view of a zoned treated microporous film suitable for use in practicing the present invention and placement of an absorbent pad thereon.
Figure 23:
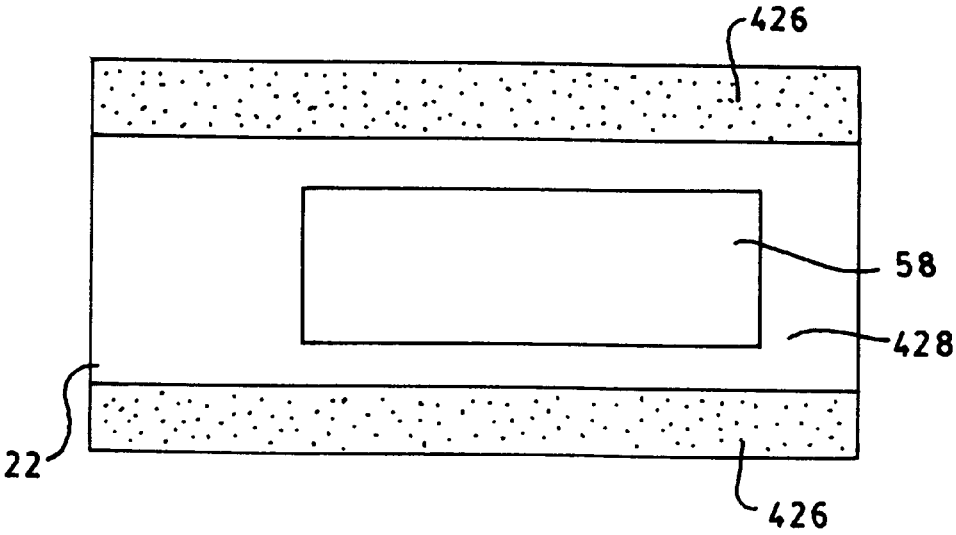
FIG. 23 is a plan view of a zoned treated microporous film suitable for use in practicing the present invention and placement of an absorbent pad thereon.
Figure 24:
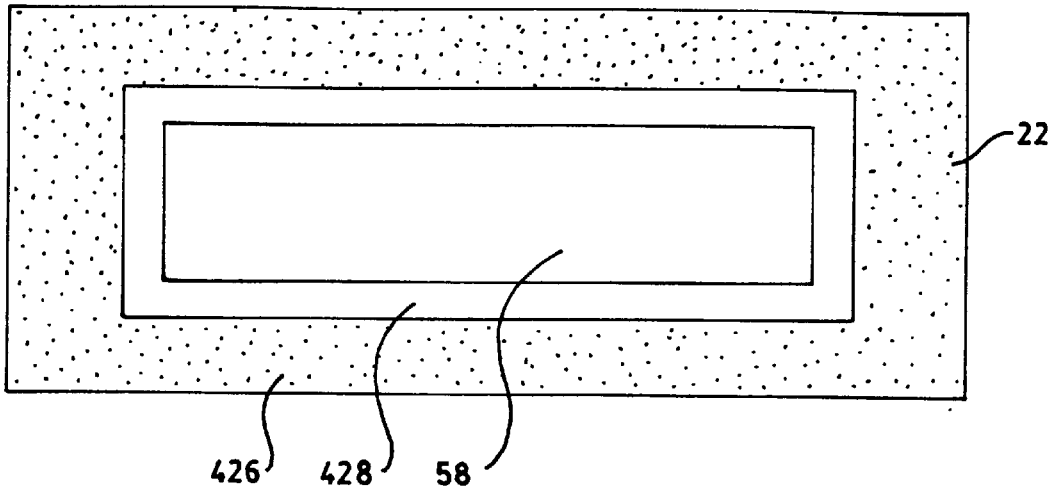
FIG. 24 is a plan view of a zoned treated microporous film suitable for use in practicing the present invention and placement of an absorbent pad thereon
Figure 25:
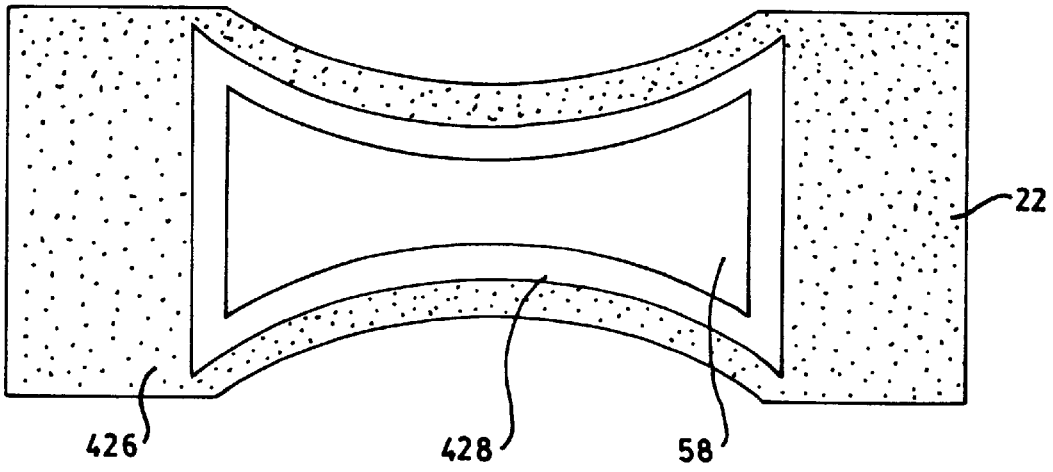
FIG. 25 is a plan view of a zoned treated microporous film suitable for use in practicing the present invention and placement of an absorbent pad thereon.

FIG. 22 shows that the absorbent pad 58 need not cover the entire second region 428 and that the absorbent pad 58 may overlap onto a portion of the first region 426. Typically the portion of the absorbent pad 58 which has the highest aqueous liquid loading is positioned over the second regions 428. FIG. 23 shows the zone treated microporous film 412 of FIGS. 15*a* and 16*a* including an absorbent pad 58 having smaller dimensions than the second region 428. FIGS. 18*a* and 20 show such a microporous film 412. FIG. 25 shows an alternative embodiment as shown in FIG. 24 including a shaped backing member 22 and absorbent pad 58 which have legcut outs typically included for improved fit and comfort of the garment 20. (See FIGS. 19*a* and 19*b*.) However, the size and/or shape of the absorbent pad 58 may coincide with the size and/or shape of the second region 428.

The regions of higher breathability extend along the outer portions or "ears" of the garment to maximize comfort and skin dryness. In a further example, the zoned breathability microporous films may be used in surgical gowns. It is believed that the regions of reduced breathability, particularly areas where breathability has been significantly or almost completely reduced, may provide improved barrier properties. For example, areas of reduced breathability are believed to provide improved barrier properties to blood borne pathogens. Thus, surgical gowns can be fabricated employing the treated or low breathability regions within high risk areas, such as the forearms of the gown, and higher WVTR regions within lower risk areas. The microporous film can also be advantageously utilized in numerous other applications employing breathable barrier fabrics.

One embodiment of the present invention is a disposable, absorbent garment 20 defining an initial expanded shape having longitudinal and transverse axes, a front waist region 37, and a back waist region 39. The front waist region 37 and the back waist region 39 is generally oppositely disposed on said longitudinal axis. A crotch region 35 is disposed between the front waist region 37 and the back waist region 39. The breathable absorbent garment 20 comprises:

a breathable film backing member 22 comprising:

a first microporous region 426 having a WVTR of at least 800 g/m$^2$/24 hours;

a second region 428 having a WVTR less than the first region 426 wherein the WVTR of the second region 428 is at least 15% less than the WVTR of the first region 426;

a aqueous liquid pervious body-side liner 40 joined to the backing member 22 approximate a periphery of the joined body-side liner 40 and the backing member 22;

a generally rectangular absorbent pad 58, having a front end edge 66, a back end edge 68 and a pair of opposing side end edges 62 and 64, positioned between the body-side liner 40 and the backing member 22 in board of the periphery of the joined body-side liner 40 and the backing member 22 and positioned generally in alignment with the second region 428 of the backing member 22; and, leg elastics 96 and 108 aligned along longitudinally extending margins of the periphery, rendering the garment 20 elastically contractible and body-conforming adjacent the crotch of a wearer.

Variations of the breathable absorbent garment of additional embodiments may include any combination of the following: The backing member 22 may be a thermoplastic polymer. The thermoplastic polymer may be a polyolefin polymer. The second region 428 of the breathable film backing member 22 may be adjacent the absorbent pad 58. The first region of the breathable film backing member 22 may be adjacent the periphery of the joined body-side liner 40 and the backing member 22. The first region 426 of the breathable film backing member 22 may be disposed in the front waist region 37 of the garment 20. The first region 426 of the breathable film backing member 22 may be disposed in the back waist region 39 of the garment 20 alone or in combination with disposition in the front waist region 37. The second region of the backing member 22 may have a minimum dimension of 3 cm by 3 cm, or more preferably, a minimum dimension of 5 cm by 5 cm. Typically, a minimum dimension is at least as large as that of the region of the absorbent pad 58 likely to get wet during use.

The first region 426 may have a WVTR in excess of 2500 g/m$^2$/24 hours and the second region 428 may have a WVTR less than 1500 g/m$^2$/24 hours and further wherein the second region 428 may comprise from about 5% to about 75% of the area of the backing member 22. The second region 428 may have a WVTR of at least about 25% less than the WVTR of the first region 426. The second region 428 may have a WVTR at least 50% less than the WVTR of the first region 426 and wherein each of said first and second regions 426 and 428 have a basis weight less than about 35 g/m$^2$. The second region 428 may have a WVTR at least about 75% less than the WVTR of the first region 426 and wherein each of the first and second regions 426 and 428 may have a basis weight less than about 35 g/m$^2$. The breathable absorbent garment 20 may further comprise a third region 429, the third region 429 may have a WVTR intermediate to the WVTR of said first region 426 and the WVTR of said second region 428 and wherein the second region 428 may comprise from about 5% to about 75% of the area of said backing member 22. The breathable absorbent garment 20 may further comprise a third region 429, the third region 429 may have a WVTR intermediate to the WVTR of the first region 426 and the second region 428 and wherein the third region 429 is contiguous with said first and second regions 426 and 428. The backing member 22 may comprise at least about 50% by weight of the thermoplastic polymer and a filler. The second region 428 may extend at least 5 cm in the cross-machine direction and may extend substantially continuously in the machine direction of the backing member 22. The second region 428 may be positioned symmetrically along the longitudinal axis of the garment 20. The backing member 22 may have a WVTR gradient.

In other embodiments, the present invention may be a disposable, breathable absorbent garment 20 defining an initial expanded shape having longitudinal and transverse axes, a front waist region 37, and a back waist region 39. The front waist region 37 and the back waist region 39 is generally oppositely disposed on the longitudinal axis. A crotch region 35 is disposed between the front waist region 37 and the back waist region 39. The breathable absorbent garment 20 comprises:

- a film backing member 22 having regions of varied breathability comprising:
  - a first microporous region 426 comprising a polyolefin polymer and a filler;
  - a second region 428 comprising a polyolefin polymer and a filler;
- wherein the first and second regions 426 and 428 comprise a continuous backing member 22 and wherein the WVTR of the second region 428 is less than the WVTR of the first region 426;
- a aqueous liquid pervious body-side liner 40 joined to the backing member 22 approximate a periphery of the joined body-side liner 40 and the backing member 22;
- a generally rectangular absorbent pad 58, having a front end edge 66, a back end edge 68 and a pair of opposing side end edges 62 and 64, positioned between the body-side liner 40 and the backing member 22 in board of the periphery of said joined body-side liner 40 and the backing member 22; and,
- leg elastics 96 and 108 aligned along longitudinally extending margins of the periphery, rendering the garment 20 elastically contractible and body-conforming adjacent the crotch of a wearer.

Various embodiments of the present invention may include any of the following: The second region 428 has a minimum dimension of 3 cm by 3 cm. The second region 428 may comprise from about 5% to about 75% of the area of the backing member 22. The first region 426 may have a WVTR between about 2000 g/m$^2$/24 hours and about 5000 g/m$^2$(24 hours and the second region 428 may have a WVTR less than about 1000 g/m$^2$/24 hours. The second region 428 may have has a WVTR less than about 1500 g/m$^2$/24 hours and the first region 426 may have a WVTR in excess of about 2500 g/m$^2$/24 hours. The second region 428 may have a WVTR less than about 800 g/m$^2$/24 hours and comprises from about 5% to about 60% of the area of the backing member 22. The first and second regions 426 and 428 may each have substantially similar basis weights. The second region 428 has a WVTR at least about 50% less than the WVTR of the first region 426 and comprises from about 5% to about 75% of the area of the backing member 22. The first and second regions 426 and 428 may comprise at least about 40% by weight of the filler. The polyolefin polymer of the first region 426 and the polyolefin polymer of the second region 428 comprise polyethylene. The polyolefin polymer of the first region 426 and the polyolefin polymer of the second region 428 comprise polypropylene. The backing member 22 may further comprise a third region 429 having a WVTR less than the WVTR of the first region 426 and greater than the WVTR of the second region 428. The third region 429 may be contiguous with the second region 428 and further wherein the second region 428 and the third region 429 together comprise from about 5% to about 75% of the area of the backing member 22. The second region 428 may have a dimension on the cross-machine direction less than the cross-machine dimension of the third region 429. The second region 428 and the third region 429 may be contiguous and further wherein the second region 428 may comprise from about 5% to about 60% of the area of the backing member 22.

Test Methods

Hydrohead: A measure of the aqueous liquid barrier properties of a fabric is the hydrohead test. The hydrohead test determines the height of water or amount of water pressure (in millibars) that the fabric will support before aqueous liquid passes therethrough. A fabric with a higher hydrohead reading indicates it has a greater barrier to aqueous liquid penetration than a fabric with a lower hydrohead. The hydrohead can be performed according to Federal Test Standard 191A, Method 5514. The hydrohead data cited herein was obtained using a test similar to the aforesaid Federal Test Standard except modified as noted below. The hydrohead was determined using a hydrostatic head tester available from Marl Enterprises, Inc. of Concord, N.C. The specimen is subjected to a standardized water pressure, increased at a constant rate until the first sign of leakage appears on the surface of the fabric in three separate areas. (Leakage at the edge, adjacent clamps is ignored.). Unsupported fabrics, such as a thin film, are supported to prevent premature rupture of the specimen.

WVTR: The water vapor transmission rate (WVTR) for the sample materials was calculated in accordance with ASTM Standard E96-80. Circular samples measuring three inches in diameter were cut from each of the test materials and a control which was a piece of CELGARD™ 2500 film from Hoechst Celanese Corporation of Sommerville, N.J. CELGARD™ 2500 film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (32° C.) or 1 hour to equilibrate. The oven was a constant temperature oven with external air circulating through it to prevent water vapor accumulation inside. A suitable forced air oven is, for example, a Blue M Power-O-Matic 60 oven distributed Blue M. Electric Company of Blue Island, Ill. Upon completion of the equilibration, the pans were removed from the oven, weighed an immediately returned to the oven. After 24 hours, the pans were removed from the oven and weighed again. The preliminary test water vapor transmission rate values were calculated with Equation (I) below:

(I) Test WVTR=(grams weight loss over 24 hours)×315.5 g/m$^2$/24 hours The relative humidity within the oven was not specifically controlled.

Under the predetermined set conditions of 100° F. (32° C.) and ambient relative humidity, the WVTR for the CELGARD™ 2500 control has been defined to be 5000 grams per square meter for 24 hours. Accordingly, the control sample was run with each test and the preliminary test values were corrected to set conditions using Equation (II) below:

(II) WVTR=(Test WVTR/control WVTR)×(5000 g/m$^2$/24 hours)

Strip Tensile: The strip tensile test measures the peak and breaking loads and peak and break percent elongations of a fabric. This test measures the load (strength) in grams and elongation in percent. In the strip tensile test, two clamps, each having two jaws with each jaw having a facing in contact with the sample, hold the material in the same plane, usually vertically, separated by 3 inches and move apart at a specified rate of extension. Values for strip tensile strength and strip elongation are obtained using a sample size of 3 inches by 6 inches, with a jaw facing size of 1 inch high by 3 inches wide, and a constant rate of extension of 300 mm/min. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154 may be used for this test. Results are reported as an average of three specimens and may be performed with the specimen in the cross direction (CD) or the machine direction (MD).

EXAMPLE I

A cast extrusion film was made, comprising LLDPE (linear low density polyethylene; 0.918 g/cm$^3$ from Dow Chemical Corp. in Midland, Mich. under the designation DOWLEX™ NAG 3310) and 48% by weight calcium carbonate (available from English China Clay America, Inc. under the designation SUPERCOAT™) coated with stearic acid. The filled film was then heated and stretched 500% its original length using a machine direction orientor unit to create a microporous film having a basis weight of approximately 14 g/m$^2$. The resulting breathable microporous film had a WVTR of 2358 g/m$^2$/24 hours, a MD strip tensile of 6987 g and a CD strip tensile of 425 g. The breathable microporous film was wound on a supply roll and subsequently unwound and fed through a pair of nip rolls at a speed of 50 feet/minute. Both rolls were steel rolls and the upper roll was patterned having configuration similar to that shown in FIGS. 1 and 3, having a raised region with a width of 8 inches that extends about the center of the roll. The lower roll was a smooth anvil roll. The nip pressure and temperature of rolls were varied in order to obtain varied levels of regional breathability, the results of which are shown on Table I.

TABLE I

| Trial | Anvil #1 Temp. (Actual) | Anvil #2 Temp. (Actual) | Nip Pressure PSIG | Nip Pressure PLI | WVTR g/m$^2$/day | Strip Tensile MD | Strip Tensile CD |
|---|---|---|---|---|---|---|---|
| 1 | 75 | 75 | 15 | 88 | 2210 | 6399 | 459 |
| 2 | 75 | 75 | 30 | 145 | 1660 | 6031 | 441 |
| 3 | 75 | 75 | 45 | 215 | 1399 | 6208 | 442 |
| 4 | 75 | 75 | 60 | 297 | 1426 | 6054 | 436 |
| 5 | 105 | 105 | 15 | 88 | 1914 | 6453 | 465 |
| 6 | 105 | 105 | 30 | 145 | 1548 | 5991 | 452 |
| 7 | 105 | 105 | 45 | 215 | 1243 | 6347 | 450 |
| 8 | 105 | 105 | 60 | 297 | 1033 | 5331 | 449 |
| 9 | 123 | 123 | 15 | 88 | 1657 | 6638 | 461 |
| 10 | 123 | 123 | 30 | 145 | 1385 | 6329 | 467 |
| 11 | 123 | 123 | 45 | 215 | 1148 | 5961 | 458 |
| 12 | 123 | 123 | 60 | 297 | 1012 | 5172 | 461 |
| 13 | 150 | 150 | 15 | 88 | 1471 | 6613 | 470 |
| 14 | 150 | 150 | 30 | 145 | 1192 | 6232 | 477 |
| 15 | 150 | 150 | 45 | 215 | 1067 | 6336 | 483 |
| 16 | 150 | 150 | 60 | 297 | 1542 | 6523 | 441 |
| 17 | 170 | 170 | 15 | 88 | 1878 | 6938 | 445 |
| 18 | 170 | 170 | 30 | 145 | 1234 | 6626 | 461 |

TABLE I-continued

| Trial | Anvil #1 Temp. (Actual) | Anvil #2 Temp. (Actual) | Nip Pressure PSIG | Nip Pressure PLI | WVTR g/m$^2$/day | Strip Tensile MD | Strip Tensile CD |
|---|---|---|---|---|---|---|---|
| 19 | 170 | 170 | 45 | 215 | 1174 | 6794 | 471 |
| 20 | 170 | 170 | 60 | 297 | 851 | 6481 | 474 |
| 21 | 195 | 195 | 15 | 88 | 970 | 6917 | 496 |
| 22 | 195 | 195 | 30 | 145 | 583 | 6800 | 503 |
| 23 | 195 | 195 | 45 | 215 | 538 | 6568 | 601 |
| 24 | 195 | 195 | 60 | 297 | 219 | 6683 | 604 |
| 25 | 220 | 220 | 15 | 88 | 185 | 6947 | 610 |
| 26 | 220 | 220 | 30 | 145 | 95 | 7308 | 737 |
| 27 | 220 | 220 | 45 | 215 | 59 | 6828 | 735 |
| 28 | 220 | 220 | 60 | 297 | 62 | 6893 | 740 |

EXAMPLE II

The stretched-filled microporous film described in Example I was laminated to a nonwoven web. The microporous film was sprayed with 3 g/m$^2$ of adhesive (amorphous polyalphaolefin adhesive available from Huntsman Polymer Corporation under the trade name RT 2730) and immediately thereafter a 17 g/m$^2$ web of polypropylene spun bond fibers was juxtaposed with and pressed against the microporous film by a pair of smooth nip rolls. The laminate was subsequently zone treated through the nip rolls described in Example I at a rate of 50 feet/minute. The resulting laminates are described in Table II. The film laminate, prior to zone treatment, had a peel strength of 860 g, a hydrohead of 162 mbar and a WVTR of 2457 g/m$^2$/24 hours.

TABLE II

| Trial | Anvil #1 Temp. (Actual) | Anvil #2 Temp. (Actual) | Nip Pressure PSIG | Nip Pressure PLI | WVTR g/m$^2$/day | Hydrohead Mbar |
|---|---|---|---|---|---|---|
| 1 | 75 | 75 | 30 | 145 | 2138 | 144 |
| 2 | 75 | 75 | 60 | 297 | 1970 | 116 |
| 3 | 130 | 130 | 30 | 145 | 1979 | 111 |
| 4 | 130 | 130 | 60 | 297 | 1521 | 111 |
| 5 | 220 | 220 | 30 | 145 | 430 | 82 |
| 6 | 220 | 220 | 60 | 297 | 347 | 52 |

EXAMPLE III

A microporous polyethylene film was laminated to a non-woven fabric to form an outer cover. Adhesive was then added to the film side of the outer cover laminate (which faces the wearer's body when incorporated in an absorbent garment) to create two breathable zones. Adhesive applied through a meltblown application at a level of 3.2 gsm was applied continuously, the full length of the article. A second adhesive head was used to apply adhesive, generally the length and width of the absorbent core, through a slot die at the same and higher add-on rates. The first adhesive system had minimal effect on the film WVTR while the second substantially reduced it. The adhesive used has designation 34-5610 from National Starch and Chemical Company in Bridgewater, N.J.

| Laminate WVTR | WVTR After Meltblown Adhesive Applic. 3.2 gsm | WVTR After Slot Coated Adhesive Applic. 3.2 gsm | WVTR After Slot Coated Adhesive Applic. 6.4 gsm |
|---|---|---|---|
| 4,136 | 3,899 | 3,087 | 2,414 |
| 4,232 | 3,933 | 3,028 | 2,332 |

(WVTR units g/m2/24 hours)

EXAMPLE IV

Figure 26:
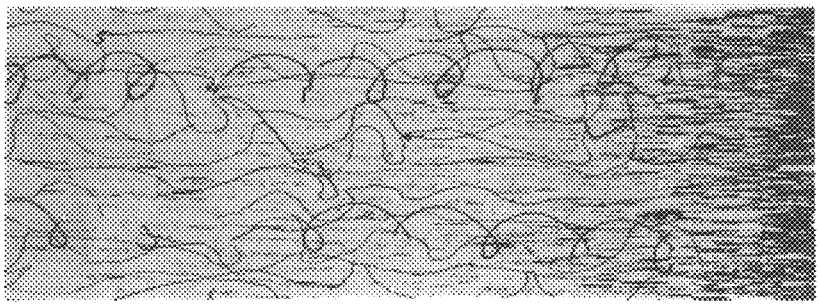
FIG. 26 is a plan view of a treated microporous film having an open adhesive pattern with minimal effect on the WVTR of the film.
Figure 27:
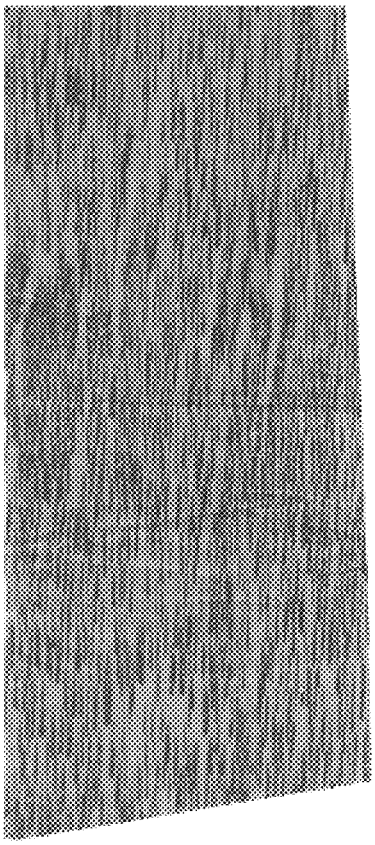
FIG. 27 is a plan view of a treated microporous film having an adhesive coat layer with significant reduction of the WVTR of the film; and, FIG. 28 is a plan view of a treated microporous film having an adhesive coat layer with significant reduction of the WVTR of the film.
Figure 28:
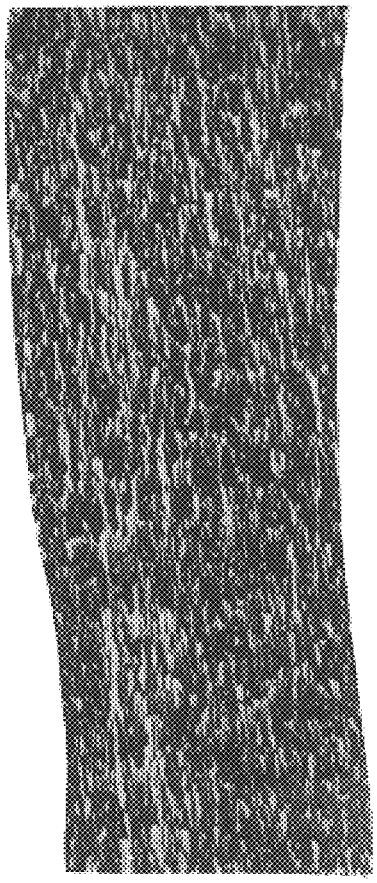

Referencing the WVTR data in Example III, FIG. 26 shows a breathable film with a meltblown adhesive coverage of about 8%. This resulted in the WVTR dropping from about 4200 to about 3900. FIG. 27 shows a breathable film with a coat layer coverage of about 24% resulting in about a 1000 drop in WVTR. FIG. 28 shows a 70% coat layer coverage which resulted in a WVTR drop of about 1800.

EXAMPLE V

It has been found that slot coating applied to a non-woven web has less effect on the laminate WVTR than applying to the film. A slot coater, therefore could be used to maintain high WVTR in the desired product regions if slot coating is applied to a non-woven like fabric rather than onto the film.

An equal amount of construction adhesive (34-5610 from National Starch and Chemical Company in Bridgewater, N.J.) was applied via slot coating onto both a non-woven fabric (0.75 osy, sheath/core, 50/50 polypropylene polyethylene spunbond) and a microporous polyethylene film with a WVTR of approximately4,270. The examples show the smaller reduction in WVTR when the non-woven was slot coated compared to when the film was slot-coated.

| Film WVTR | Laminate WVTR When Slot Coated onto Non-woven | Laminate WVTR | WVTR When Slot Coated onto Film |
|---|---|---|---|
| 4,270 | 4,080 | 4,080 | 3,500 |

EXAMPLE VI

It has been found that neither a meltblown (also referred to as MB) nor swirl adhesive application lower the WVTR of the microporous film significantly at adhesive levels up to 3.2 gsm of 34-5610 adhesive.

| Description | WVTR |
|---|---|
| Film | 4,266 |
| 3.2 gsm MB on nonwoven | 4,178 |
| 1.6 gsm MB on film | 4,317 |
| 3.2 gsm Swirl on film | 4,063 |
| 1.0 gsm Swirl on film | 4,486 |

EXAMPLE VII

This example demonstrates that high WVTR values can result in condensation of wter vapor on the outer surface of an absorbent garment. This is perceived as leakage by many consumers.

Panelists evaluated the materials in a blind comparison using the following test method. Before evaluation, all samples were loaded with 240 mls of body temperature saline, and placed on a heating pad also warmed to body temperature for two hours, Each diaper was placed inside a black box for a blind evaluation. All participants evaluated each material four times as presented to them in a randomly ordered sequence. Each material by feeling it was evaluated inpendently. Each of the two studies included three codes. In each study panelists evaluated a total of twelve diapers (3 codes×4 repeats=12 diapers) with a fifteen minute break after evaluating six diapers to help reduce hand fatigue.

| Product | WVTR of Outer Cover | Front Moisture Rating | Back Moisture Rating |
|---|---|---|---|
| A | 1,650 | 15.9 | 22.1 |
| B | 2,715 | 18.8 | 24.1 |
| C | 4,125 | 20.9 | 26.3 |
| D | 0 | 12 | 18 |

Products A, B, C, and D were commercially available diapers in which the outer covers were replaced with over covers having the stated WVTR.

EXAMPLE VIII

This example demonstrates that high WVTR levels in nonabsorbent areas of a disposable garment increase wearer comfort. The disposable garments tested were commercially available DEPENDS Undergarments. The test was conducted on a KES-F7 Thermo-Lobo IIB Type equipment available from Kato-Tech Co., LTD., in Kyoto, Japan. The test method is described in the operating manual for the equipment. Outer covers of differing breathability were tested.

The ability of moisture and heat to permeate through fabric is a significant factor in determining how comfortable a garment will be. Heat can be transferred through a fabric in two ways: dry heat transfer and/or moisture-assisted heat transfer. From the dry and wet heat transfer rate measurements, the permeability index (Im), can be calculated. The KES Thermo-labo test measures the dry and wet heat transfer rates of a material using a guarded or sweating hot plate. It also measures how warm or cool a material feels to the touch and the thermal conductivity of materials.

The characteristic values shown from the KES Thermo-labo test are described below.

Wet Heat Transfer represents the amount of heat that is transferred from the skin through the fabric to the outside environment with the assistance of moisture. The larger the wet heat transfer value, the more heat will be lost or transferred through the fabric with the assistance of moisture. This test is appropriate for the measurement of heat transfer in most situations where the wearer would perspire.

Im or Permeability Index is the ratio of the thermal and evaporative resistance of the fabric to the ratio of thermal and evaporative resistance of air. As the value approaches 1, the less resistant or more air-like the fabric is. For example, a lightweight, loosely woven fabric would have a larger Im value than Tyvek. (Differences as small as 0.01 can be perceived.)

| | Non-breathable non-micro-porous film | 1,200 WVTR microporous film | 2,500 WVTR microporous film | 3.5 osy woven cotton |
|---|---|---|---|---|
| Wet Heat Transfer (Watts/m$^2$) | 7.72 | 8.87 | 11.94 | 18.4 |
| Im or Permeability Index | 0.18 | 0.23 | 0.39 | 0.59 |

EXAMPLE IX

This example demonstrates that high WVTR levels in certain areas of a disposable garment increase wearer skin wellness by reducing skin occlusion and excessive hydration of the skin.

Undergarments that were modifications of commercially available DEPEND® Undergarments, were tested with 20 panelists. The modifications included shortening the absorbent pad from 21 inches to 19 inches (centered on the outer cover) and incorporating new outer covers with the stated WVTRs. The outer covers consisted of a film (either non-porous or microporous) and a nonwoven laminated to the film.

Skin conductance measurements were taken on the panelist's lower back in a region where the garment's body-side liner and outer cover covered the skin (not in a region where the absorbent pad was present).

The skin conductance readings were taken with a Skicon 200 instrument such as that available from ACA DERM of Mento Park, Calif. Panelists were given a short sleeve disposable lab coat, made of polypropylene spunbond, cotton sweatpants, and a pair of cotton underwear to wear during the test period. Panelists were then allowed to acclimate to the environment which was controlled to approximately 72° F./43% R. H. for 10–15 minutes. After acclimation, the panelists lay on their stomachs, their clothing over their lower back was peeled down, and a Baseline skin conductance reading was taken using the Skicon.

Subsequently, the panelists were given an undergarment to don, under their underwear and sweatpants. The total wear time of the undergarment was 1.5 hours. During the first ten minutes of wear time, the panelists participated in a moderate exercise of their choice (such as walking, threadmill, stationary bike, aerobic activity). The next twenty minutes, the panelists rested. They exercised the next ten minutes (30–40 minutes into wear time), rested the next 20 minutes (40–60 minutes into wear time), exercised the next ten minutes (60–70 minutes into wear time), and finally rested the last twenty minutes of the 1.5 hour undergarment weartime.

After the 1.5 hour wear time, a post-wear skin conductance reading was taken in the same manner and region as the baseline reading.

The change in skin conductance, from the baseline to post wear regions, represents the change in skin hydration during that period. The data shows that the non-breathable product resulted in a much greater increase in skin hydration than the breathable products. Such increases over time lead to wearer discomfort and reduced skin wellness.

| | Baseline Skin Surface Moisture Reading | Post wear Skin Surface Moisture Reading | Change in Skin Surface Moisture Reading after Wear Time |
|---|---|---|---|
| Non breathable non-microporous film | 220 | 1,187 | 967 |
| 2,500 WVTR microporous film | 222 | 376 | 154 |
| 3,700 WVTR microporous film | 239 | 364 | 125 |

While various patents and other reference materials have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A disposable, breathable absorbent garment defining an initial expanded shape having longitudinal and transverse axes, a front waist region, a back waist region, said front waist region and said back waist region being generally oppositely disposed on said longitudinal axis and a crotch region disposed between said front waist region and said back waist region and comprising:

a breathable film backing member comprising:

a first microporous region having a WVTR of at least 800 g/m$^2$/24 hours;

a second region having a WVTR less than said first region wherein the

WVTR of said second region is at least 15% less than said WVTR of said first region;

a aqueous liquid pervious body-side liner joined to said backing member approximate a periphery of said joined body-side liner and said backing member;

a generally rectangular absorbent pad, having a front end edge, a back end edge and a pair of opposing side end edges, positioned between said body-side liner and said backing member in board of the periphery of said joined body-side liner and backing member; and, leg elastics aligned along longitudinally extending margins of said periphery, rendering said garment elastically contractible and body-conforming adjacent the crotch of a wearer.

2. The garment of claim 1, wherein said backing member is a thermoplastic polymer.

3. The garment of claim 1, wherein said second region of said breathable film backing member is adjacent said absorbent pad.

4. The garment of claim 3, wherein said backing member is a thermoplastic polymer.

5. The garment of claim 1, wherein said first region of said breathable film backing member is disposed in said front waist region of said garment.

6. The garment of claim 5, wherein said backing member is a thermoplastic polymer.

7. The garment of claim 1, wherein said first region of said breathable film backing member is disposed in said back waist region of said garment.

8. The garment of claim 7, wherein said backing member is a thermoplastic polymer.

9. The garment of claim 1, wherein said first region of said breathable film backing member is disposed in said front waist region and said back waist region of said garment.

10. The garment of claim 3, wherein said backing member is a thermoplastic polymer.

11. The garment of claims 2, wherein said second region of said backing member has a minimum dimension of 3 cm by 3 cm.

12. The garment of claims 3, wherein said second region of said backing member has a minimum dimension of 5 cm by 5 cm.

13. The garment of claim 2, wherein said thermoplastic polymer is a polyolefin polymer.

14. The garment of claim 4, wherein said thermoplastic polymer is a polyolefin polymer.

15. The garment of claim 1, wherein said first region has a WVTR in excess of 2500 $g/m^2/24$ hours and said second region has a WVTR less than 1500 $g/m^2/24$ hours and further wherein said second region comprises from about 5% to about 75% of the area of said backing member.

16. The garment of claim 2, wherein said second region has a WVTR at least about 25% less than the WVTR of said first region and wherein each of said first and second regions have a basis weight less than about 35 $g/m^2$.

17. The garment of claim 16, wherein said first region has a thickness less than about 95% of the thickness of said second region and said second region comprises from about 5% to about 75% of the area of said backing member.

18. The garment of claim 2, wherein said second region has a WVTR at least 50% less than the WVTR of said first region and wherein each of said first and second regions have a basis weight less than about 35 $g/m^2$.

19. The garment of claim 18, wherein said first region is less than 90% of the thickness of said second region and wherein the basis weight of said first and second regions are substantially similar.

20. The garment of claim 2, wherein said second region has a WVTR at least about 75% less than the WVTR of said first region and wherein each of said first and second regions have a basis weight less than about 35 $g/m^2$.

21. The garment of claim 1, further comprising a third region, said third region having a WVTR intermediate to the WVTR of said first region and the WVTR of said second region and wherein said second region comprises from about 5% to about 75% of the area of said backing member.

22. The garment of claim 18, further comprising a third region, said third region having a WVTR and thickness intermediate to the WVTR and thickness of said first region and said second region and wherein said third region is contiguous with said first and second regions.

23. The garment of claim 2, wherein said backing member comprises at least about 50% by weight of said thermoplastic polymer and a filler.

24. The garment of claim 1, wherein said second region extends at least 5 cm in the cross-machine direction and extends substantially continuously in the machine direction of said backing member.

25. The garment of claim 1, wherein said second region is positioned symmetrically along the longitudinal axis of said garment.

26. The garment of claim 25, wherein said backing member has a WVTR gradient.

27. A disposable, breathable absorbent garment defining an initial expanded shape having longitudinal and transverse axes, a front waist region, a back waist region, said front waist region and said back waist region being generally oppositely disposed on said longitudinal axis and a crotch region disposed between said front waist region and said back waist region and comprising:

a film backing member having regions of varied breathability comprising:

a first microporous region comprising a polyolefin polymer and a filler;

a second region comprising a polyolefin polymer and a filler;

wherein said first and second regions comprise a continuous backing member and wherein the WVTR of said second region is less than the WVTR of said first region and the thickness of said first region is less than the thickness of said second region;

a aqueous liquid pervious body-side liner joined to said backing member approximate a periphery of said joined body-side liner and said backing member;

a generally rectangular absorbent pad, having a front end edge, a back end edge and a pair of opposing side end edges, positioned between said body-side liner and said backing member in board of the periphery of said joined body-side liner and backing member; and, leg elastics aligned along longitudinally extending margins of said periphery, rendering said garment elastically contractible and body-conforming adjacent the crotch of a wearer.

28. The garment of claim 27, wherein said first and second regions have a basis weight less than about 35 $g/m^2$ and said second region has a minimum dimension of 3 cm by 3 cm.

29. The garment of claim 28, wherein said second region comprises from about 5% to about 75% of the area of the backing member.

30. The garment of claim 29, wherein said first region has a WVTR between about 2000 $g/m^2/24$ hours and about 5000 $g/m^2/24$ hours and said second region has a WVTR less than about 1000 $g/m^2/24$ hours.

31. The garment of claim 29, wherein said second region has a WVTR less than about 1500 $g/m^2/24$ hours and said first region has a WVTR in excess of about 2500 $g/m^2/$ 24 hours.

32. The garment of claim 30, wherein said second region has a WVTR less than about 300 $g/m^2/24$ hours and comprises from about 5% to about 60% of the area of said backing member.

33. The garment of claim 28, wherein said first and second regions each have substantially similar basis weights.

34. The garment of claim 27, wherein said second region has a WVTR at least about 50% less than the WVTR of said first region and comprises from about 5% to about 75% of the area of said backing member.

35. The garment of claim 29, wherein said first and second regions comprise at least about 40% by weight of filler.

36. The garment of claim 35, wherein said polyolefin polymer of said first region and said polyolefin polymer of said second region comprise polyethylene.

37. The garment of claim 35, wherein said polyolefin polymer of said first region and said polyolefin polymer of said second region comprise polypropylene.

38. The garment of claim 28, wherein said backing member further comprises a third region having a WVTR less than the WVTR of said first region and greater than the WVTR of said second region.

39. The garment of claim 38, wherein said third region is contiguous with said second region and further wherein said second and third regions together comprise from about 5% to about 75% of the area of said backing member.

40. The garment of claim 38, wherein said second region has a dimension on the cross-machine direction less than the cross-machine dimension of said third region.

41. The garment of claim 40, wherein said second and third regions are contiguous and further wherein aid second region comprises from about 5% to about 60% of the area of said backing member.

* * * * *